US011124845B2

(12) United States Patent
Pomper et al.

(10) Patent No.: US 11,124,845 B2
(45) Date of Patent: Sep. 21, 2021

(54) PSMA-BASED MOLECULAR-GENETIC REPORTER SYSTEM

(71) Applicant: THE JOHNS HOPKINS UNIVERSITY, BALTIMORE, MD (US)

(72) Inventors: Martin G. Pomper, Baltimore, MD (US); Mark Castanares, Balitmore, MD (US); Il Minn, Ellicott City, MD (US); Shawn Lupold, Ellicott City, MD (US)

(73) Assignee: The Johns Hopkins university, Baltimore, MD (US)

( * ) Notice: Subject to any disclaimer, the term of this patent is extended or adjusted under 35 U.S.C. 154(b) by 0 days.

(21) Appl. No.: 15/126,749

(22) PCT Filed: Mar. 18, 2015

(86) PCT No.: PCT/US2015/021233
§ 371 (c)(1),
(2) Date: Sep. 16, 2016

(87) PCT Pub. No.: WO2015/143029
PCT Pub. Date: Sep. 24, 2015

(65) Prior Publication Data
US 2017/0218464 A1 Aug. 3, 2017

Related U.S. Application Data

(60) Provisional application No. 61/972,833, filed on Mar. 31, 2014, provisional application No. 61/954,947, filed on Mar. 18, 2014.

(51) Int. Cl.
*C12N 15/85* (2006.01)
*C12Q 1/6897* (2018.01)
*A61K 51/04* (2006.01)
*G01N 33/574* (2006.01)
*A61K 49/00* (2006.01)
*C07K 14/005* (2006.01)
*C12N 9/48* (2006.01)
*C12N 15/86* (2006.01)

(52) U.S. Cl.
CPC ........ *C12Q 1/6897* (2013.01); *A61K 49/0021* (2013.01); *A61K 51/0406* (2013.01); *A61K 51/0455* (2013.01); *C07K 14/005* (2013.01); *C12N 9/485* (2013.01); *C12N 15/85* (2013.01); *C12N 15/86* (2013.01); *C12Y 304/17021* (2013.01); *G01N 33/57434* (2013.01); *G01N 33/57492* (2013.01); *G01N 33/57496* (2013.01); *C12N 2710/10043* (2013.01); *C12N 2710/10044* (2013.01); *C12N 2710/10071* (2013.01); *C12N 2710/16143* (2013.01); *C12N 2710/16222* (2013.01); *C12N 2830/60* (2013.01); *G01N 2333/705* (2013.01); *G01N 2458/00* (2013.01)

(58) Field of Classification Search
None
See application file for complete search history.

(56) References Cited

U.S. PATENT DOCUMENTS

| | | | | |
|---|---|---|---|---|
| 8,435,777 B1* | 5/2013 | Reynes | ............... | C12Y 113/12 435/189 |
| 9,695,248 B2* | 7/2017 | Maddon | ............ | A61K 38/1709 |
| 2003/0059942 A1 | 3/2003 | Cho et al. | | |
| 2004/0219677 A1* | 11/2004 | Drocourt | .............. | C07K 14/245 435/488 |
| 2013/0263296 A1 | 10/2013 | Pomper et al. | | |

OTHER PUBLICATIONS

Yao et al (The Prostate, 2009, pp. 1-12).*
Castanares (Dissertation, 2012. AAI3528545, Diss. Abstr. Int., B 2013, 74 Development and application of a reporter-probe system based on the Prostate Specific Membrane Antigen).*
Bhang et al (Nature Medicine, 2009. vol. 17, No. 1, pp. 123-130).*
Koster et al (Developmental Biology, 2001, vol. 233, pp. 329-346).*
Min et al (Biomaterials, 2005. vol. 26, pp. 1063-1070).*
International Search Report and Written Opinion dated Jun. 3, 2015, from related PCT Patent Application No. PCT/US15/021233.
Asakawa, K. et al., "Targeted gene expression by the Gal4-UAS system in zebrafish," Development, Growth & Differentiation, Aug. 2008, vol. 50, No. 6, pp. 391-399.
Osborne, J. et al., "Prostate-specific membrane antigen-based imaging," Urologic Oncology, Feb. 2013, vol. 31, No. 2, pp. 144-154.
Castanares, M. et al., "Evaluation of prostate-specific membrane antigen as an imaging reporter," Journal of Nuclear Medicine, Epub. Apr. 3, 2014, vol. 55, No. 5, pp. 805-811.
Afshar-Oromieh et al., PET imaging with a [68Ga]gallium-labelled PSMA ligand for the diagnosis of prostate cancer: biodistribution in humans and first evaluation of tumour lesions. Eur J Nucl Med Mol Imaging. Apr. 2013;40(4):486-95.
Anilkumar et al., Prostate-specific membrane antigen association with filamin A modulates its internalization and NAALADase activity. Cancer Research. 2003, 63(10):2645-2648.
Banerjee et al., A modular strategy to prepare multivalent inhibitors of prostate-specific membrane antigen (PSMA). Oncotarget. Dec. 2011;2(12):1244-53.
Banerjee et al., Sequential SPECT and optical imaging of experimental models of prostate cancer with a dual modality inhibitor of the prostate-specific membrane antigen. Angew Chem Int Ed Engl. Sep. 19, 2011;50(39):9167-70.
Barrett et al., First-in-man evaluation of 2 high-affinity PSMA-avid small molecules for imaging prostate cancer. J Nucl Med. Mar. 2013;54(3):380-7.

(Continued)

Primary Examiner — Celine X Qian
(74) Attorney, Agent, or Firm — Casimir Jones, S.C.; Jeffrey W. Childers

(57) ABSTRACT

The presently disclosed subject matter provides methods, reporter gene constructs, and kits for using prostate-specific membrane antigen (PSMA) as an imaging reporter to image a variety of cells and tissues.

17 Claims, 17 Drawing Sheets
Specification includes a Sequence Listing.

(56) References Cited

OTHER PUBLICATIONS

Barton et al., Phase I study of noninvasive imaging of adenovirus-mediated gene expression in the human prostate. Mol Ther. Oct. 2008;16(10):1761-9.

Bauer et al., Human TLR9 confers responsiveness to bacterial DNA via species-specific CpG motif recognition. Proc Natl Acad Sci U S A. Jul. 31, 2001;98(16):9237-42.

Beeres et al., Role of imaging in cardiac stem cell therapy. J Am Coll Cardiol. Mar. 20, 2007;49(11):1137-48.

Brader et al., Noninvasive molecular imaging using reporter genes. J Nucl Med. Feb. 2013;54(2):167-72.

Campbell et al., Structure-guided engineering of human thymidine kinase 2 as a positron emission tomography reporter gene for enhanced phosphorylation of non-natural thymidine analog reporter probe. J Biol Chem. Jan. 2, 2012;287(1):446-54.

Chang et al., Prostate-specific membrane antigen is produced in tumor-associated neovasculature. Clin Cancer Res. Oct. 1999;5(10):2674-81.

Chen et al., 2-(3-{1-Carboxy-5-[(6-[18F]fluoropyridine-3-carbonyl)-amino]-pentyl}-ureido)-pentanedioic acid, [18F]DCFPyL, a PSMA-based PET imaging agent for prostate cancer. Clin Cancer Res. 2011, 17(24):7645-7653.

Chen et al., A low molecular weight PSMA-based fluorescent imaging agent for cancer. Biochem. Biophys. Res. Comm. 2009, 390(3):624-629.

Chen et al., Radiohalogenated prostate-specific membrane antigen (PSMA)-based ureas as imaging agents for prostate cancer. J. Med. Chem. 2008, 51(24):7933-7943.

Cho et al., Biodistribution, tumor detection, and radiation dosimetry of 18F-DCFBC, a low-molecular-weight inhibitor of prostate-specific membrane antigen, in patients with metastatic prostate cancer. J Nucl Med. 2012, 53(12):1883-1891.

De La Vieja et al., Molecular analysis of a congenital iodide transport defect: G543E impairs maturation and trafficking of the Na+/I-symporter. Mol. Endocrinol. 2005, 19(11):2847-2858.

Dingli et al., Combined I-124 positron emission tomography/computed tomography imaging of NIS gene expression in animal models of stably transfected and intravenously transfected tumor. Mol Imaging Biol. 2006; 8(1):16-23.

FDA. Points to consider on plasmid DNA vaccines for preventive infectious disease indications. Center for Biologics Evaluation and Research 1996; 2 Pages.

Forss-Petter et al., Transgenic mice expressing betagalactosidase in mature neurons under neuron-specific enolase promoter control. Neuron 1990, 5:187-197.

Gil et al., A method to rapidly and accurately compare the relative efficacies of noninvasive imaging reporter genes in a mouse model and its application to luciferase reporters. Mol Imaging Biol. 2012, 14(4):462-471.

Grant et al., Prostate specific membrane antigen (PSMA) regulates angiogenesis independently of VEGF during ocular neovascularization. PloS One 2012, 7(7):e41285.

Heston, Characterization and glutamyl preferring carboxypeptidase function of prostate specific membrane antigen: a novel folate hydrolase. Urology 1997, 49(3A Suppl):104-112.

Hoti et al., Androgen receptor attenuation of Ad5 replication: implications for the development of conditionally replication competent adenoviruses. Mol Ther. 2007, 15(8):1495-1503.

Johnson et al., Differential biodistribution of adenoviral vector in vivo as monitored by bioluminescence imaging and quantitative polymerase chain reaction. Hum. Gene Ther. 2006; 17(12):1262-1269.

Likar et al., A new pyrimidine-specific reporter gene: a mutated human deoxycytidine kinase suitable for PET during treatment with acycloguanosine-based cytotoxic drugs. J Nucl Med. 2010, 51(9):1395-1403.

Liu et al., Constitutive and antibody-induced internalization of prostate-specific membrane antigen. Cancer Res. 1998, 58(18):4055-4060.

Luo et al., A protocol for rapid generation of recombinant adenoviruses using the AdEasy system. Nature Protocols. 2007, 2(5):1236-1247.

Mease et al., N-[N-[(S)-1,3-Dicarboxypropyl]carbamoyl]-4-]18F]fluorobenzyl-L-cysteine, [18F]DCFBC: a new imaging probe for prostate cancer. Clin Cancer Res. 2008; 14(10):3036-3043.

Min et al., Comparison of [18F]FHBG and [14C]FIAU for imaging of HSV1-tk reporter gene expression: adenoviral infection vs stable transfection. Eur. J. Nucl. Med. Mol. I. 2003, 30(11):1547-1560.

Miyagawa et al., Non-invasive imaging of cardiac transgene expression with PET: comparison of the human sodium/iodidesymporter gene and HSV1-tk as the reporter gene. Eur. J. Nucl. Med. Mol. I. 2005; 32(9):1108-1114.

Mlcochova et al., Prostate-specific membrane antigen and its truncated form PSM'. The Prostate. 2009, 69(5):471-479.

Overbeek et al., Lens-specific expression and developmental regulation of the bacterial chloramphenicol acetyltransferase gene driven by the murine alpha A-crystallin promoter in transgenic mice. Proc. Natl. Acad. Sci. U.S.A. 1985, 82:7815-7819.

Ponde et al., Rapid and reproducible radiosynthesis of [18F] FHBG. Nucl. Med. Biol. 2004, 31(1):133-138.

Ponomarev et al., A human-derived reporter gene for noninvasive imaging in humans: mitochondrial thymidine kinase type 2. J Nucl Med. 2007; 48(5):819-826.

Rajasekaran et al., A novel cytoplasmic tail MXXXL motif mediates the internalization of prostate-specific membrane antigen. Mol. Biol. Cell 2003; 14(12):4835-4845.

Rajasekaran et al., Is prostate-specific membrane antigen a multifunctional protein? Am. J. Physiol. 2005, 288(5):C975-981.

Tjuvajev et al., Comparison of radiolabeled nucleoside probes (FIAU, FHBG, and FHPG) for PET imaging of HSV1-tk gene expression. J Nucl Med. 2002; 43(8):1072-1083.

Van Der Woude et al., Novel pyridinium surfactants for efficient, nontoxic in vitro gene delivery. Proc Natl Acad Sci USA 1997, 94:1160-1165.

Yaghoubi et al., Human pharmacokinetic and dosimetry studies of [(18)F]FHBG: a reporter probe for imaging herpes simplex virus type-1 thymidine kinase reporter gene expression. J Nucl Med. 2001, 42(8):1225-1234.

Yaghoubi et al., Measuring herpes simplex virus thymidine kinase reporter gene expression in vitro. Nat. Protoc. 2006, 1(4):2137-2142.

Yaghoubi et al., Positron emission tomography reporter genes and reporter probes: gene and cell therapy applications. Theranostics 2012, 2(4):374-391.

* cited by examiner

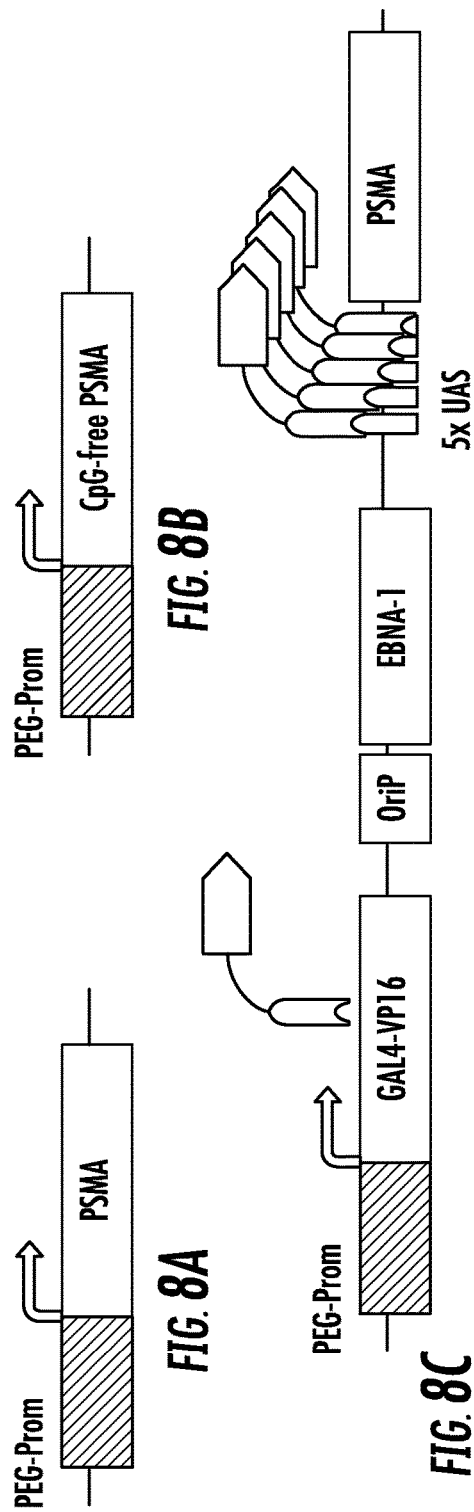
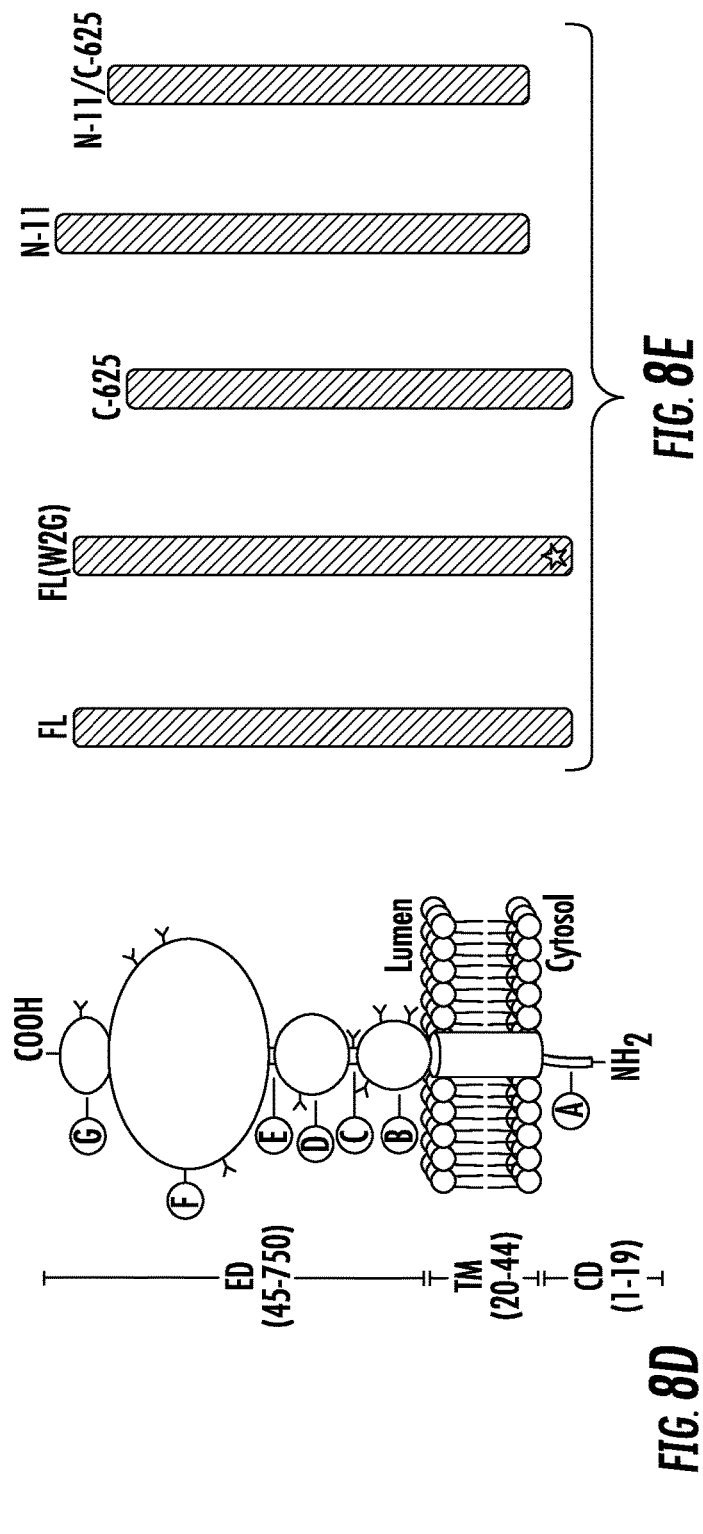
FIG. 8A
FIG. 8B
FIG. 8C
FIG. 8D
FIG. 8E

ATGTGGAATCTCCTTCATGAAACAGACTCTGCTGTGGCCACAGCCAGAAGACCCAGATGG
CTGTGTGCTGGGGCCCTGGTGCTGGCTGGTGGCTTCTTTCTCCTGGGCTTCCTCTTTGGG
TGGTTTATAAAATCCTCCAATGAAGCTACTAACATTACTCCAAAGCATAATATGAAAGCA
TTTTTGGATGAATTGAAAGCTGAGAACATCAAGAAGTTCTTATATAATTTTACACAGATA
CCACATTTAGCAGGAACAGAACAAAACTTTCAGCTTGCAAAGCAAATTCAATCCCAGTGG
AAAGAATTTGGCCTGGATTCTGTTGAGCTAGCACATTATGATGTCCTGTTGTCCTACCCA
AATAAGACTCATCCCAACTACATCTCAATAATTAATGAAGATGGAAATGAGATTTTCAAC
ACATCATTATTTGAACCACCTCCTCCAGGATATGAAAATGTTTCTGATATTGTACCACCT
TTCAGTGCTTTCTCTCCTCAAGGAATGCCAGAGGGAGATCTAGTGTATGTTAACTATGCA
AGAACTGAAGACTTCTTTAAATTGGAAAGGGACATGAAAATCAATTGCTCTGGGAAAATT
GTAATTGCCAGATATGGGAAAGTTTTCAGAGGAAATAAGGTTAAAAATGCCCAGCTGGCA
GGGGCCAAAGGAGTCATTCTCTACTCTGACCCTGCTGACTACTTTGCTCCTGGGGTGAAG
TCCTATCCAGATGGTTGGAATCTTCCTGGAGGTGGTGTCCAGAGAGGAAATATCCTAAAT
CTGAATGGTGCAGGAGACCCTCTCACACCAGGTTACCCAGCAAATGAATATGCTTATAGG
AGAGGAATTGCAGAGGCTGTTGGTCTTCCAAGTATTCCTGTTCATCCAATTGGATACTAT
GATGCACAGAAGCTCCTAGAAAAAATGGGTGGCTCAGCACCACCAGATAGCAGCTGGAGA
GGAAGTCTCAAAGTGCCCTACAATGTTGGACCTGGCTTTACTGGAAACTTTTCTACACAA
AAAGTCAAGATGCACATCCACTCTACCAATGAAGTGACAAGAATTTACAATGTGATAGGT
ACTCTCAGAGGAGCAGTGGAACCAGACAGATATGTCATTCTGGGAGGTCACAGGGACTCA
TGGGTGTTTGGTGGTATTGACCCTCAGAGTGGAGCAGCTGTTGTTCATGAAATTGTGAGG
AGCTTTGGAACACTGAAAAGGAAGGGTGGAGACCTAGAAGAACAATTTTGTTTGCAAGC
TGGGATGCAGAAGAATTTGGTCTTCTTGGTTCTACTGAGTGGGCAGAGGAGAATTCAAGA
CTCCTTCAAGAGAGGGGAGTGGCTTATATTAATGCTGACTCATCTATAGAAGGAAACTAC
ACTCTGAGAGTTGATTGTACACCCCTGATGTACAGCTTGGTACACAACCTAACAAAGAG
CTGAAAAGCCCTGATGAAGGCTTTGAAGGCAAATCTCTTTATGAAAGTTGGACTAAAAAA

*FIG. 12*

AGTCCTTCCCCAGAGTTCAGTGGCATGCCCAGGATAAGCAAATTGGGATCTGGAAATGAT
TTTGAGGTGTTCTTCCAAAGACTTGGAATTGCTTCAGGCAGAGCAAGGTATACTAAAAAT
TGGGAAACAAACAAATTCAGTGGCTATCCACTGTATCACAGTGTCTATGAAACATATGAG
TTGGTGGAAAAGTTTTATGATCCAATGTTTAAATATCACCTCACTGTGGCCCAGGTTAGA
GGAGGGATGGTGTTTGAGCTAGCCAATTCCATAGTGCTCCCTTTTGATTGTAGAGATTAT
GCTGTAGTTTTAAGAAAGTATGCTGACAAAATCTACAGTATTTCTATGAAACATCCACAG
GAAATGAAGACATACAGTGTATCATTTGATTCACTTTTTTCTGCAGTAAAGAATTTTACA
GAAATTGCTTCCAAGTTCAGTGAGAGACTCCAGGACTTTGACAAAAGCAACCCAATAGTA
TTAAGAATGATGAATGATCAACTCATGTTTCTGGAAAGAGCATTTATTGATCCATTAGGG
TTACCAGACAGGCCTTTTTATAGGCATGTCATCTATGCTCCAAGCAGCCACAACAAGTAT
GCAGGGGAGTCATTCCCAGGAATTTATGATGCTCTGTTTGATATTGAAAGCAAAGTGGAC
CCTTCCAAGGCCTGGGGAGAAGTGAAGAGACAGATTTATGTTGCAGCCTTCACAGTGCAG
GCAGCTGCAGAGACTTTGAGTGAAGTAGCCTAA

FIG. 12 (cont.)

PSMA-BASED MOLECULAR-GENETIC REPORTER SYSTEM

CROSS-REFERENCE TO RELATED APPLICATIONS

This application is a 35 U.S.C. § 371 National Stage Entry of International Application No. PCT/US15/021233 having an international filing date of Mar. 18, 2015, which claims the benefit of U.S. Provisional Application No. 61/954,947, filed Mar. 18, 2014, and U.S. Provisional Application No. 61/972,833, filed Mar. 31, 2014, which are incorporated herein by reference in their entirety.

FEDERALLY SPONSORED RESEARCH OR DEVELOPMENT

This invention was made with government support under EB005324 awarded by the National Institutes of Health. The government has certain rights in the invention.

INCORPORATION-BY-REFERENCE OF MATERIAL SUBMITTED ELECTRONICALLY

This application contains a sequence listing. It has been submitted electronically via EFS-Web as an ASCII text file entitled "111232-00553_ST25.txt". The sequence listing is 8,192 bytes in size, and was created on Sep. 16, 2016. It is hereby incorporated by reference in its entirety.

BACKGROUND

Reporter gene imaging is a component of molecular imaging that can provide noninvasive assessments of endogenous biologic processes in living subjects and that can be performed using different imaging modalities (Brader et al., 2013). Reporter genes were first developed using the bacterial β-galactosidase and chloramphenicol acetyltransferase genes to study various cellular processes both in vitro and in vivo (Forss et al., 1990; Overbeek et al. 1985). Visualization of these first reporter enzymes required postmortem tissue sampling and processing (Forss et al., 1990; Overbeek et al. 1985), but advances in cell biology led to the development of novel noninvasive visualization systems that could provide accurate and sensitive measurements in animal models of human disease (Brader et al., 2013). In particular, gene reporter-probe systems currently offer a non-invasive means to monitor gene therapy, to track the movement of cells or the activation of signal transduction pathways, and to study protein-protein interactions and other aspects of signal transduction (Brader et al., 2013).

A number of reporter genes, including the mutant herpes simplex virus thymidine kinase (HSV-sr39tk) and the human sodium iodide symporter (hNIS) have been clinically applied (Barton et al. 2008; Yaghoubi et al., 2001). However, in general, current reporter-probe systems still face limitations for clinical translation. Such limitations include, for example, the lack of biocompatibility due to immunogenicity, low sensitivity due to insufficient reporter expression per cell or lack of a signal amplification mechanism, and high background due to non-specific binding of probe.

SUMMARY

In one aspect, the presently disclosed subject matter provides a method for using prostate-specific membrane antigen (PSMA) as an imaging reporter, the method comprising: a) introducing a reporter gene construct comprising a PSMA gene operably linked to a transcriptional promoter to a cell; b) allowing the cell to express PSMA protein; c) adding an imaging probe that can detect the PSMA protein to the cell; and d) imaging the imaging probe, thereby detecting the PSMA protein.

In certain aspects, the presently disclosed subject matter provides an adenoviral reporter gene construct comprising a prostate-specific membrane antigen (PSMA) gene operably linked to a cytomegalovirus immediate-early gene (CMV) promoter.

In other aspects, the presently disclosed subject matter provides a non-viral, episomal reporter gene construct comprising a prostate-specific membrane antigen (PSMA) gene operably linked to a PEG-Promoter.

In further aspects, the presently disclosed subject matter provides a kit comprising a presently disclosed construct.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE DRAWINGS

Figure 2:
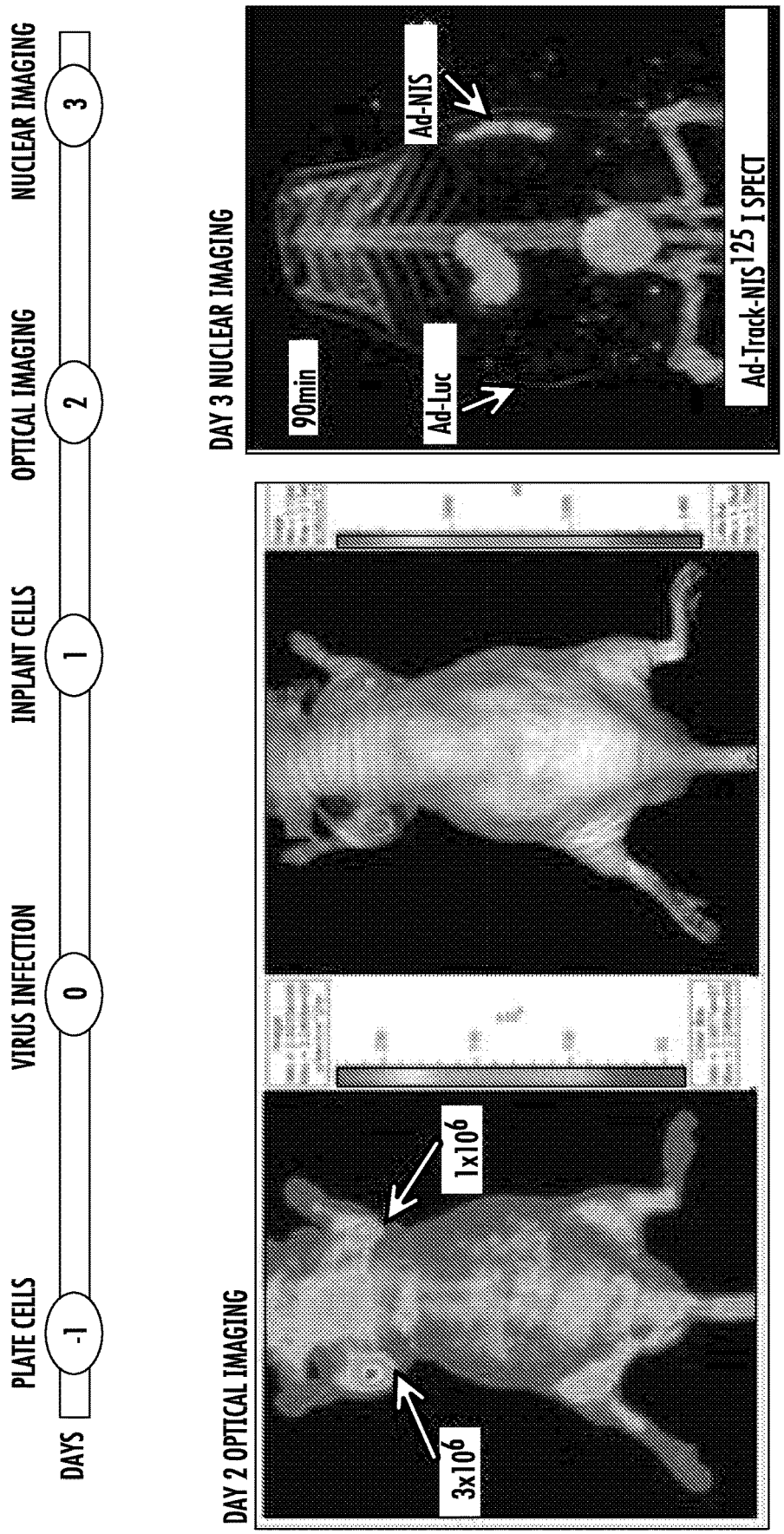
Figure 3:
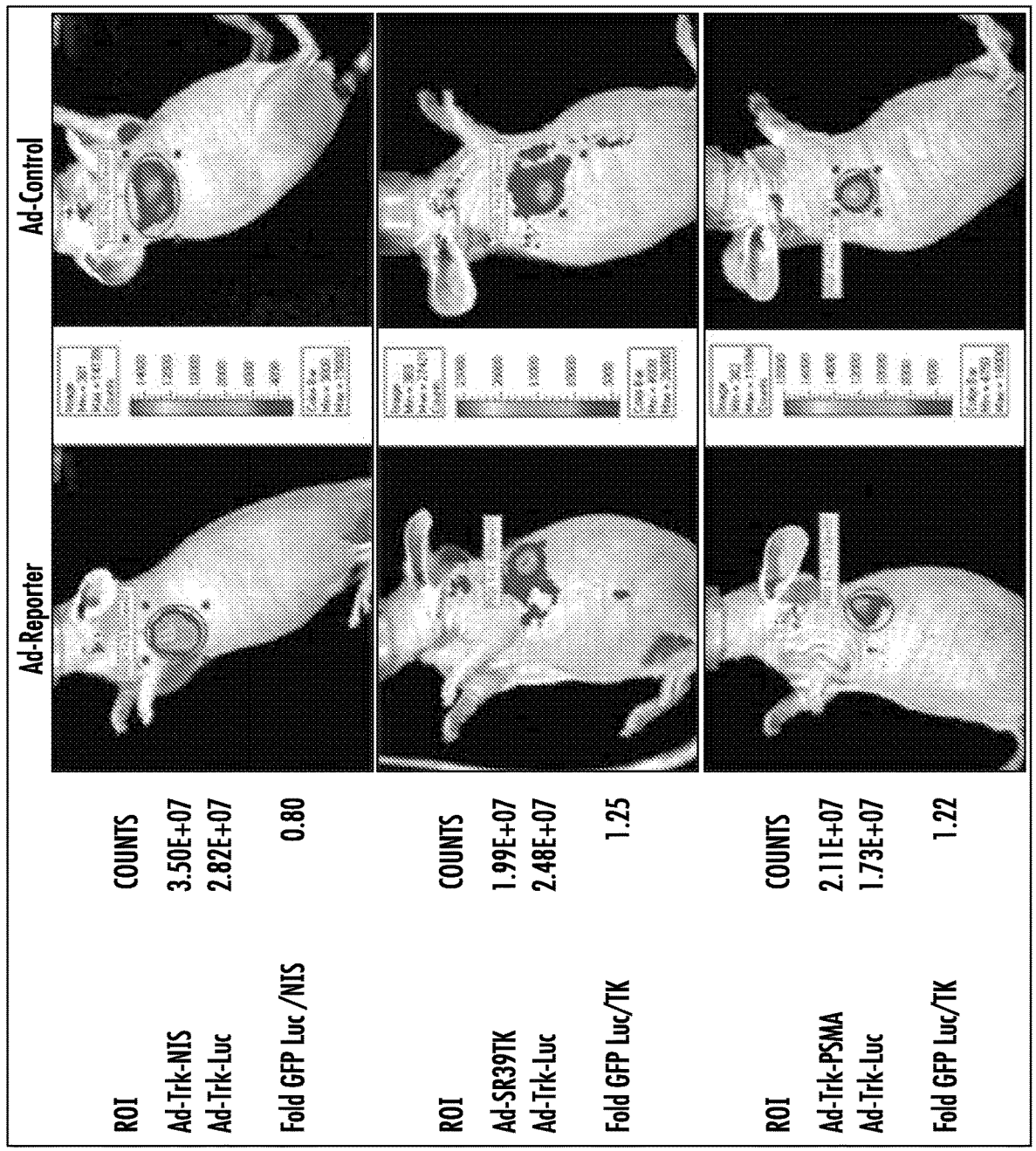
Figure 5A:
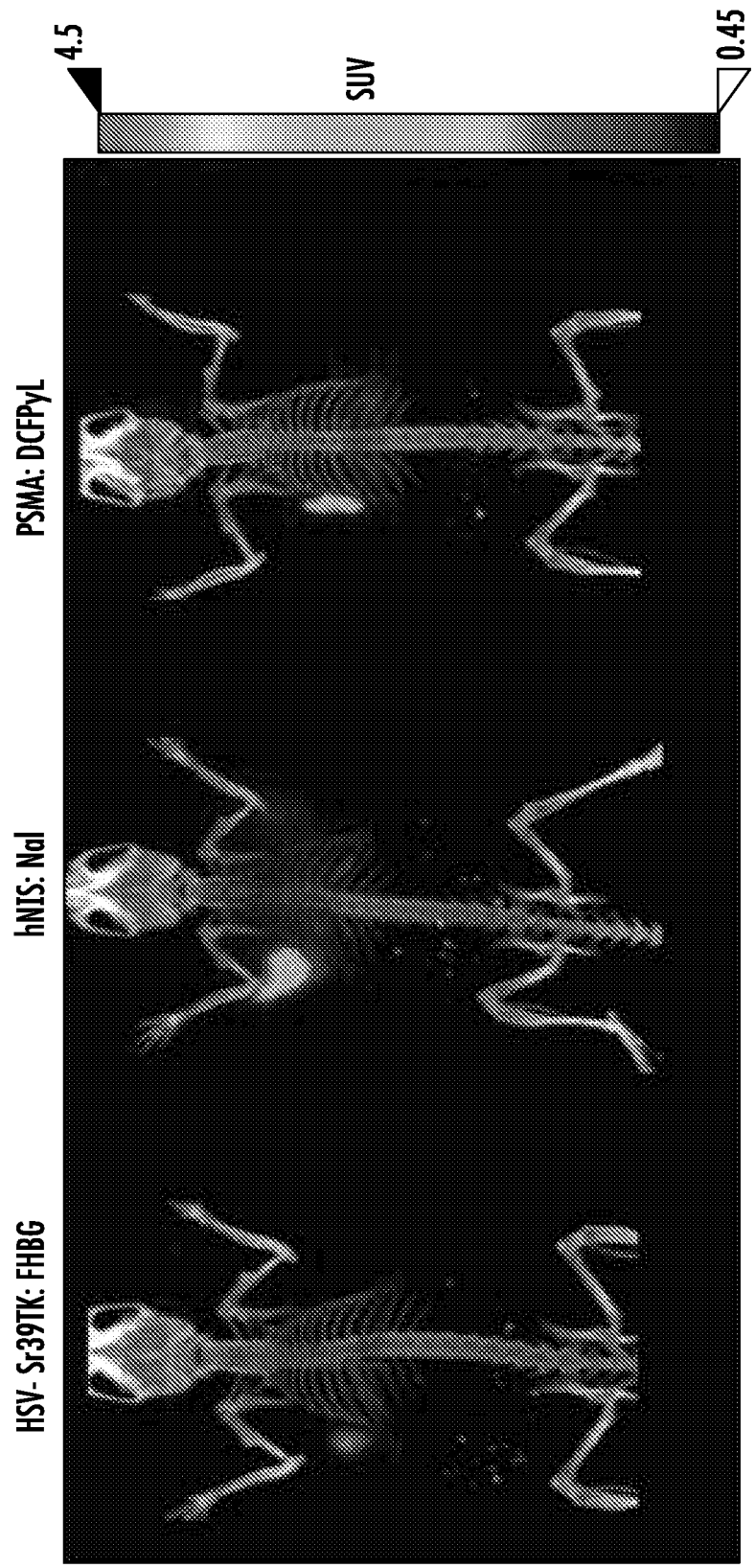
Figure 5B:
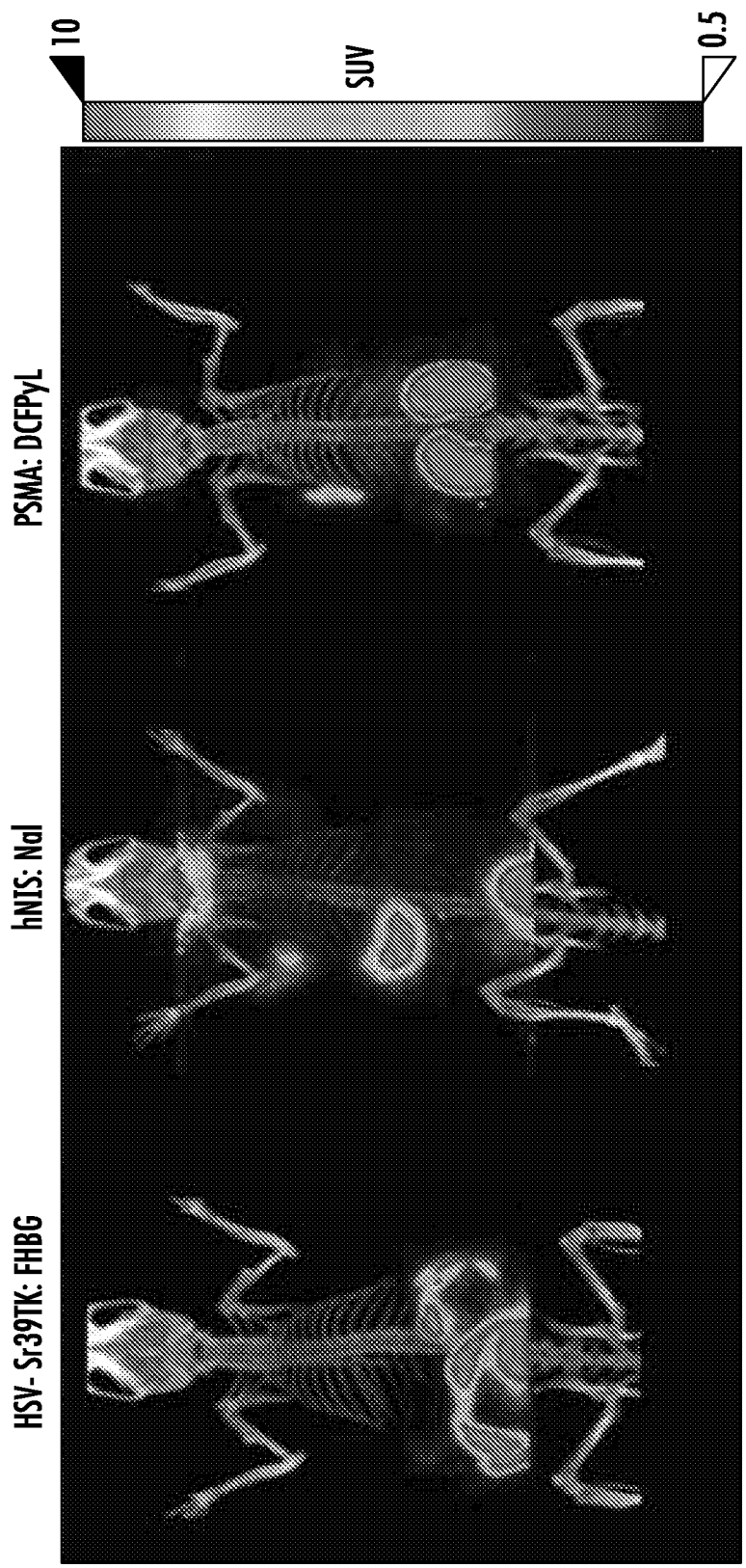
Figure 6A:
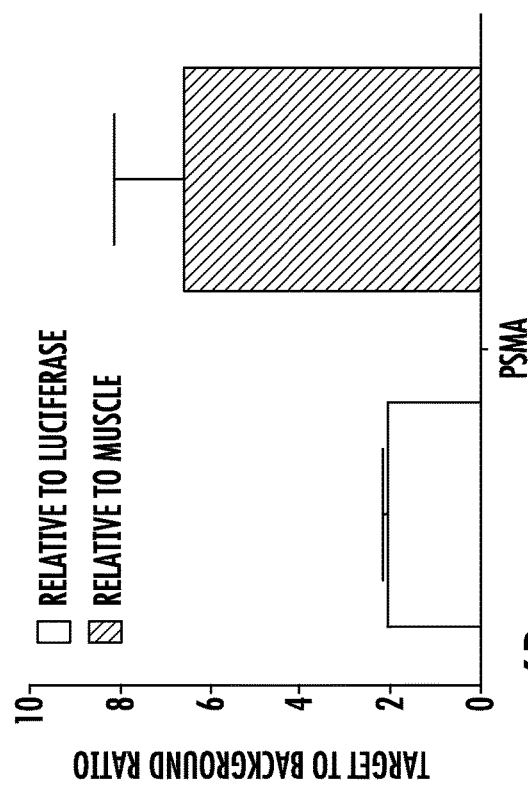
Figure 6B:
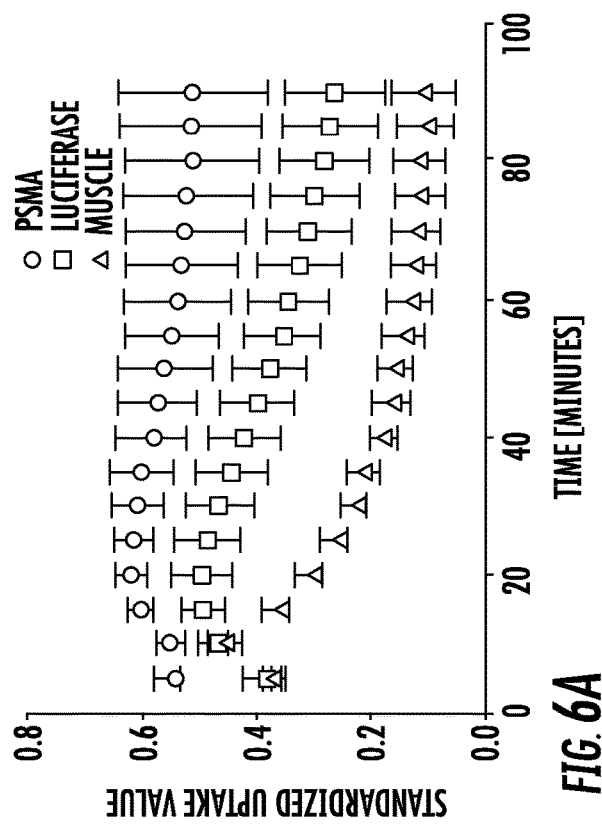
Figure 6C:
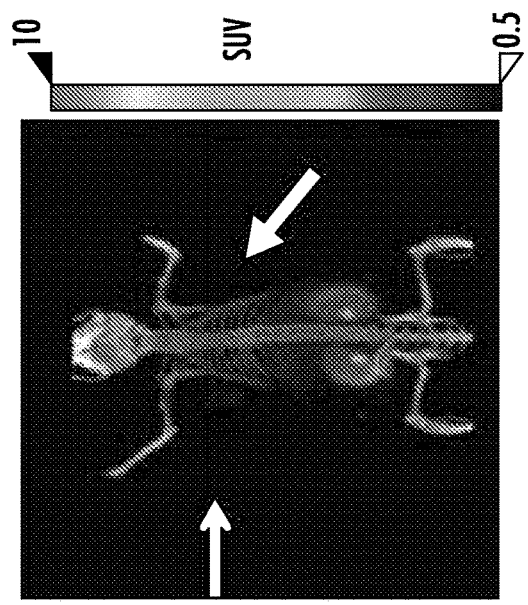
Figure 6D:
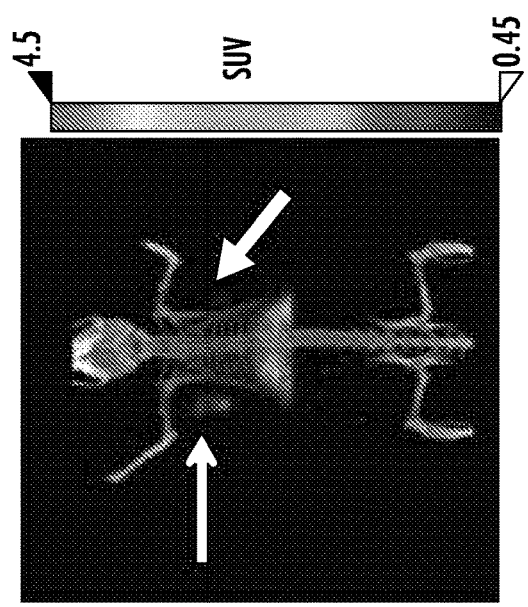
Figure 7A:
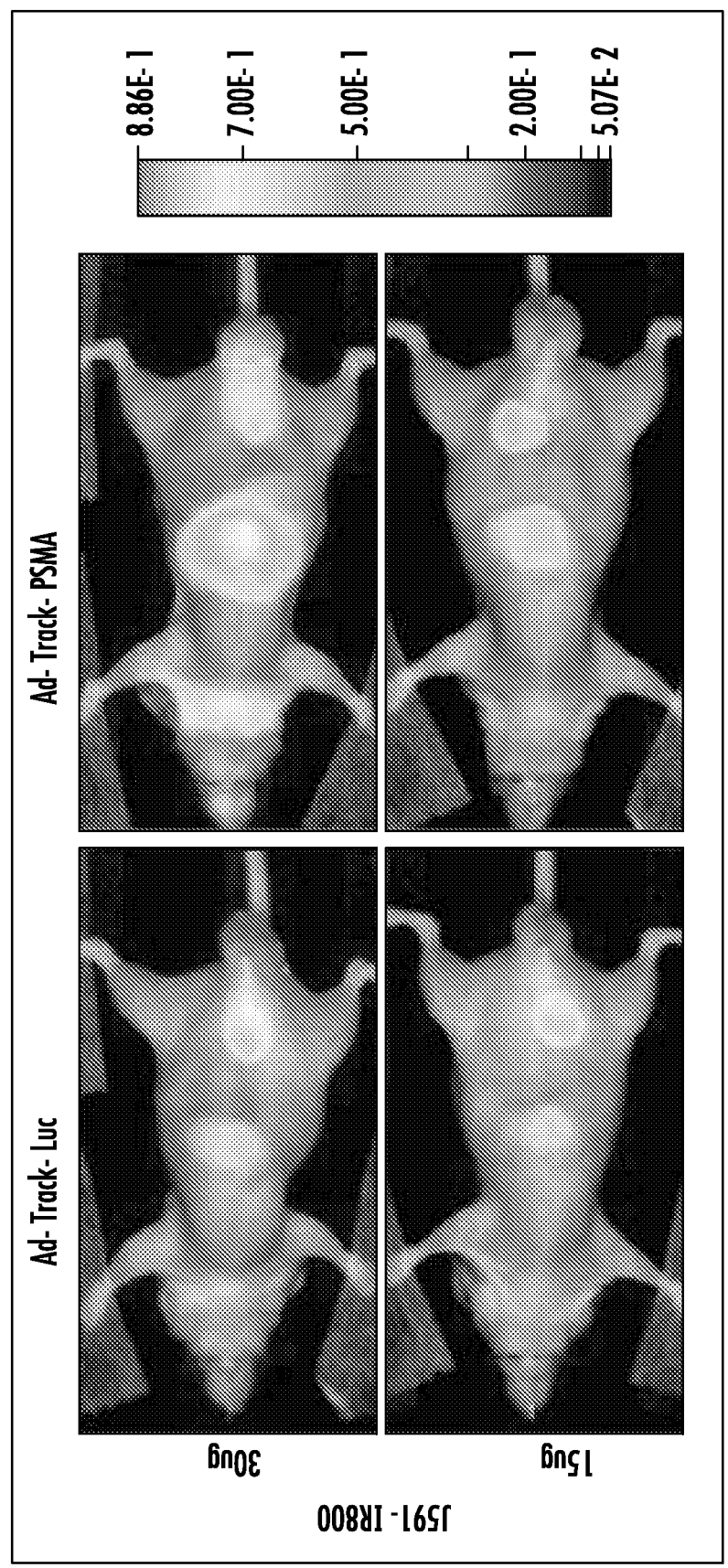
Figure 7B:
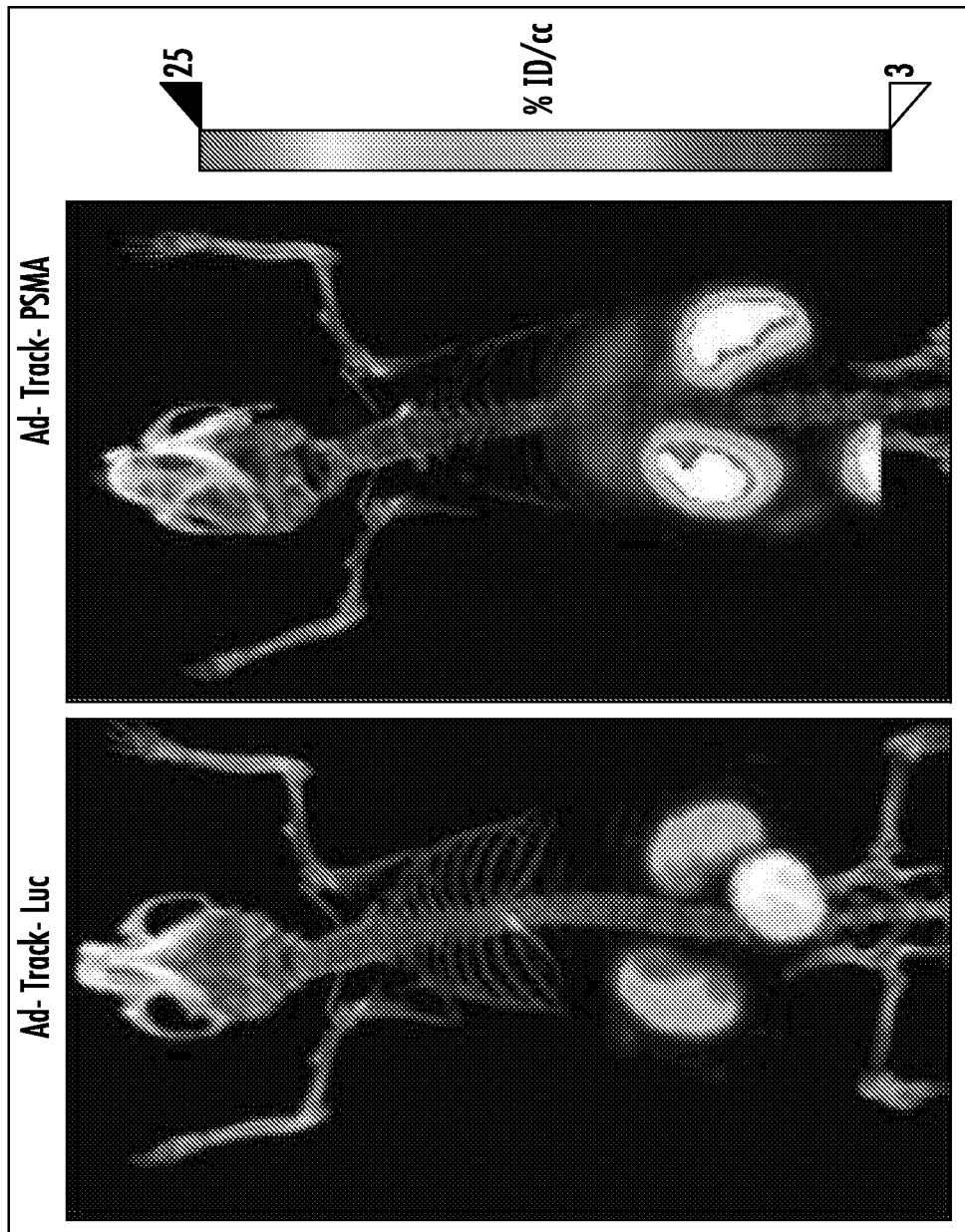
Figure 9A:
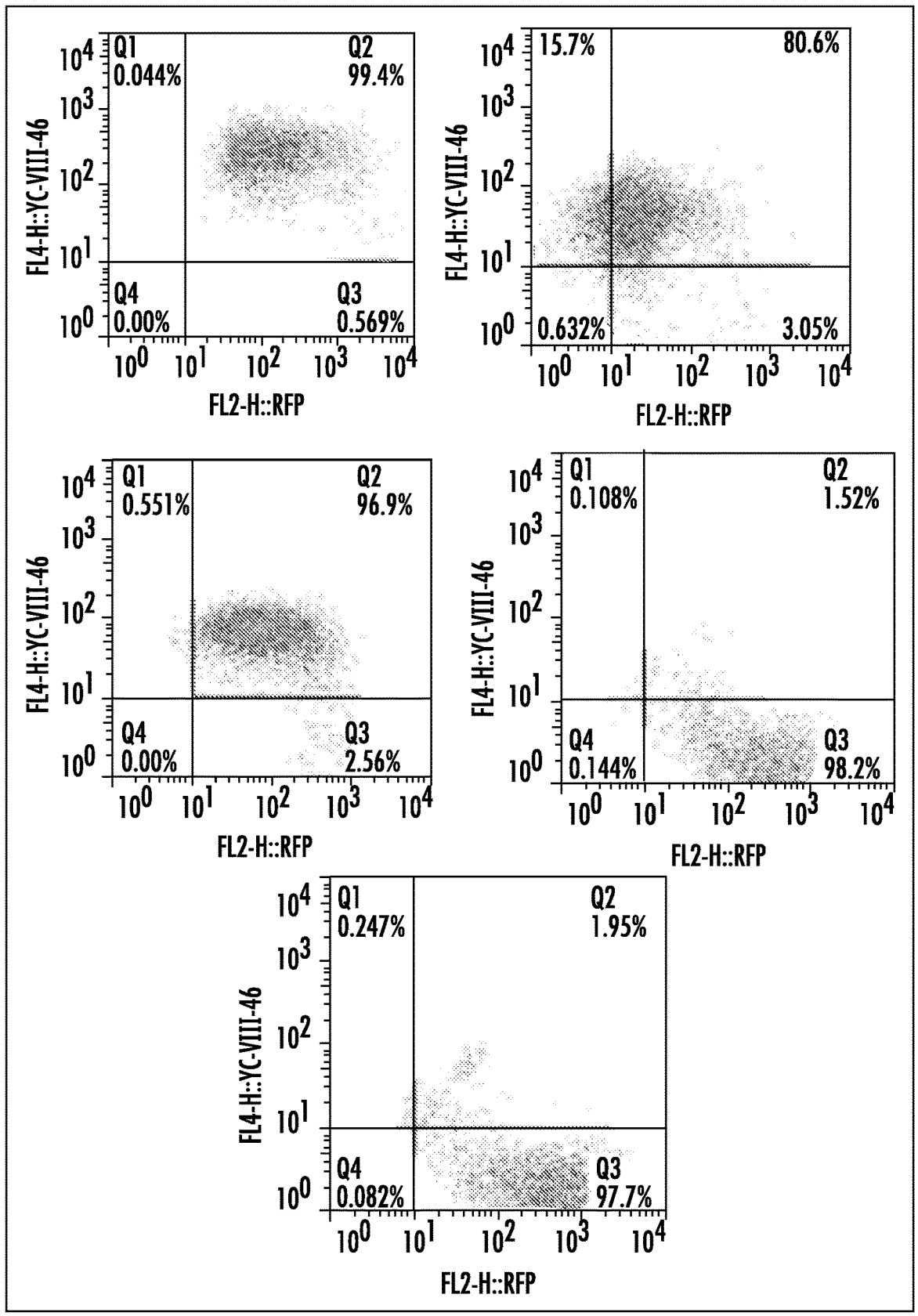
Figure 9B:
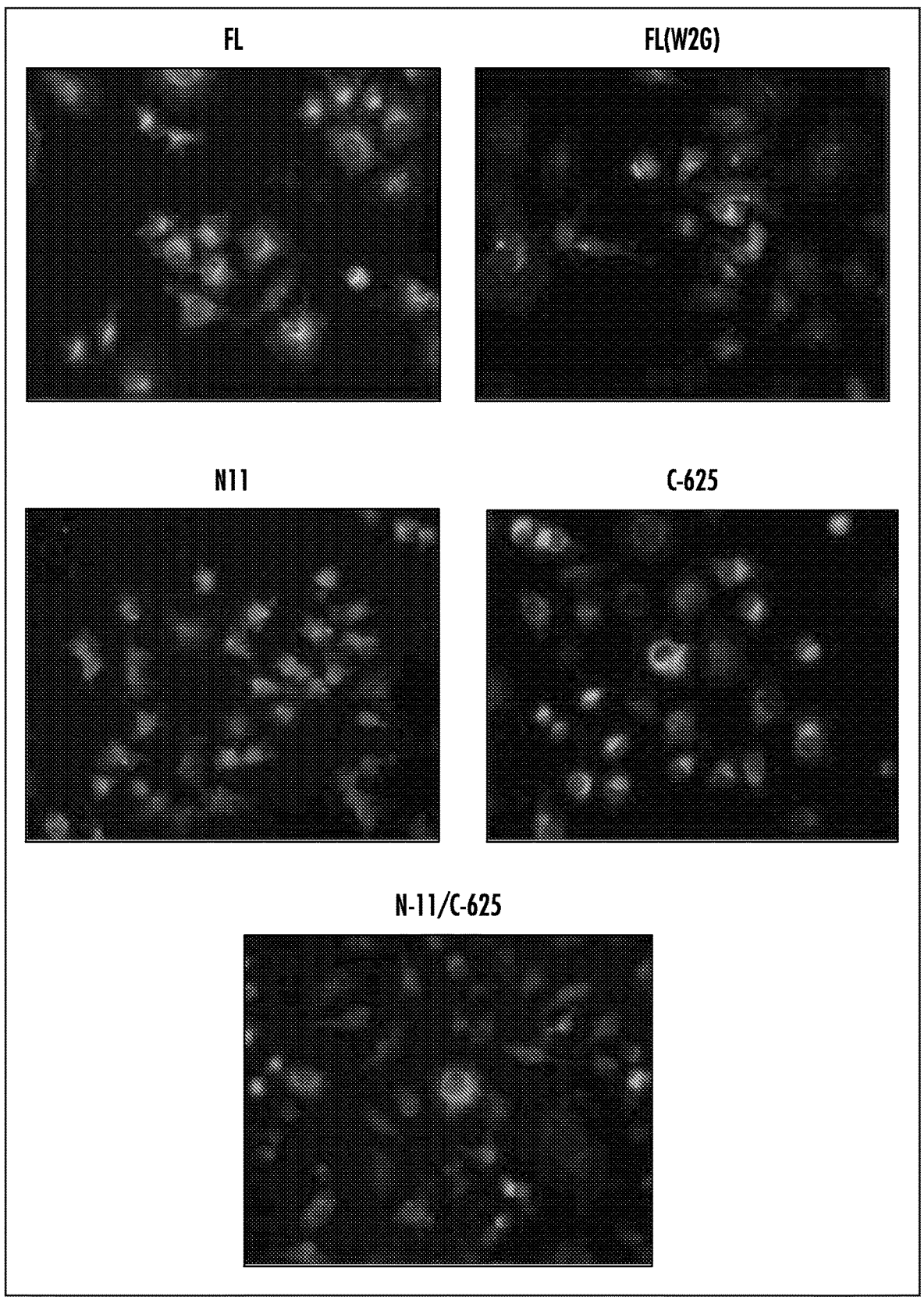
Figure 10:
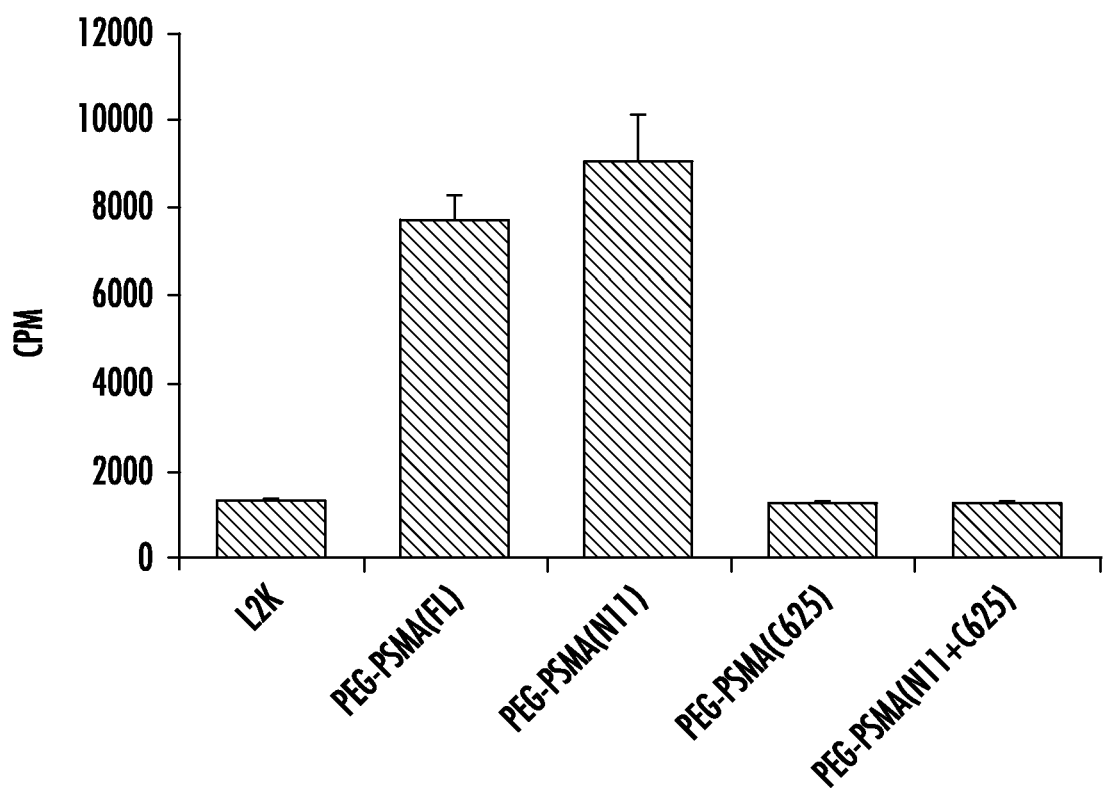
Figure 11:
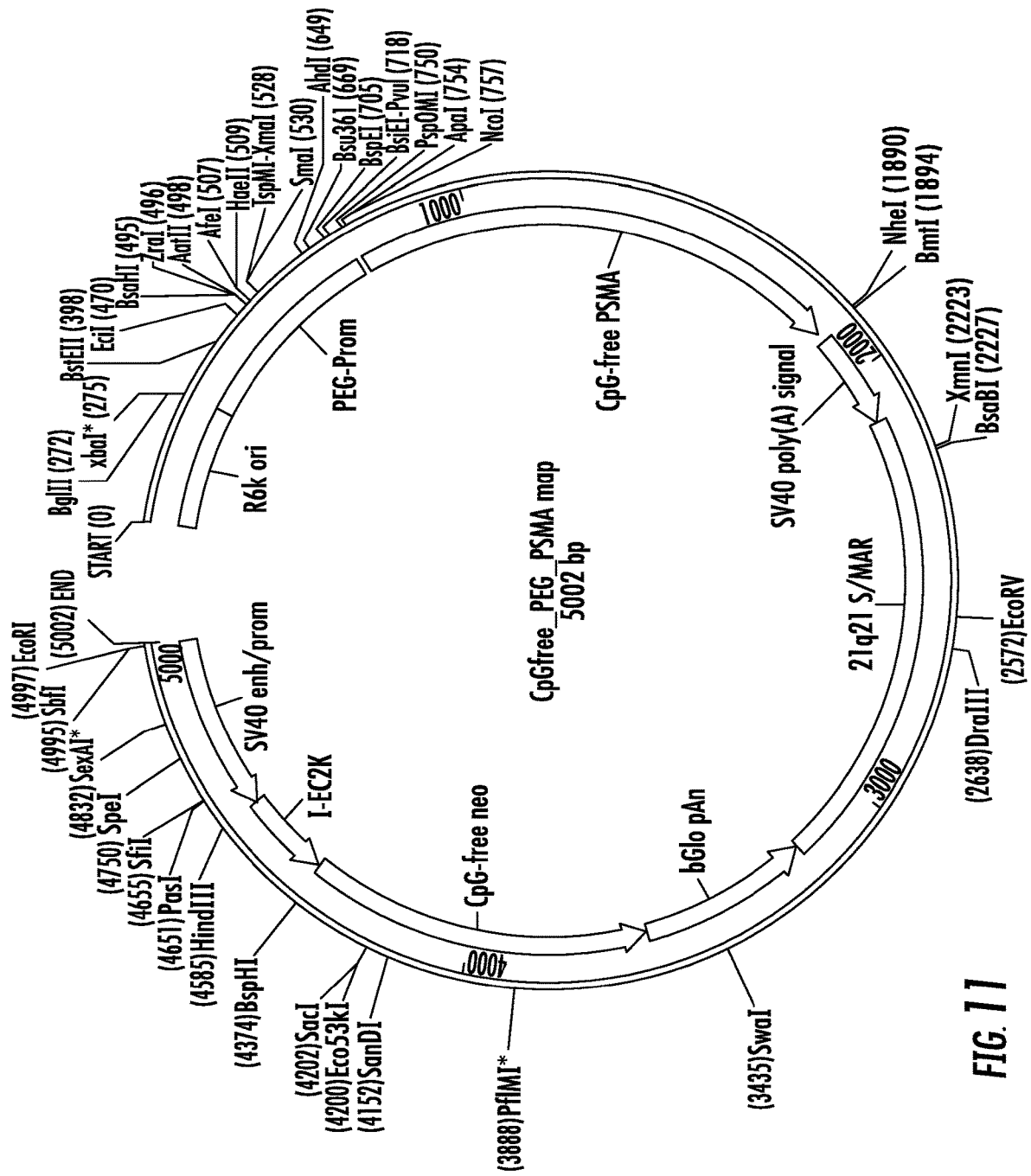

Having thus described the presently disclosed subject matter in general terms, reference will now be made to the accompanying Figures, which are not necessarily drawn to scale, and wherein:

FIGS. 1A-1D show in vitro characterization of reporter adenovirus: (A) reporter expression was validated by western blot in HCT116 cells and by fluorescent cellular immunoassay in PC3-CAR cells 48 hours after infection of reporter adenovirus; and functionality of each reporter was verified in HCT116 and PC3-CAR cells by (B) [$^3$H]GCV uptake, (C) $^{125}$I uptake, and (D) YC-I-27 binding. Data were normalized to cellular GFP expression and plotted as mean±standard error of the mean of 3 replicates. *P<0.01;

FIG. 2 shows in vivo GFP imaging of PC3-CAR cells infected in vitro with equal MOI of a PET imaging reporter or control adenovirus (AdTrack-Luciferase), separately mixed with matrigel, and implanted contralaterally into the upper flanks of a nude mouse (24 hours post-infection);

FIG. 3 shows the bioluminescent imaging of the matrigel suspension model from FIG. 2;

FIGS. 4A-4G show in vivo comparison of imaging reporters: time-activity curves for respective reporter-probe systems in matrigel suspension model for: (A) HSV-sr39TK: FHBG; (B) hNIS:$^{125}$I; and (C) PSMA:DCFPyL. Reporter derived signal-to-control and reporter derived signal-to-muscle ratios for: (D) HSV-sr39TK; (E) hNIS; and (F) PSMA systems. (G) Peak signal-to-noise ratios of each reporter-probe pair where compared. Data are mean±standard error of the mean of four animals. *P<0.05;

FIGS. 5A-5B show PET/CT imaging of reporter-probe systems in which representative maximum intensity projections of reporter-probe systems of data were collected from 60-90 min after radiotracer injection and images were cropped above the liver and below the thyroid to display the ability of each reporter to sequester its respective probe (A); and uncropped images demonstrate background associated with each reporter-probe system (B). All images were decay corrected and scaled to the same maximum value;

FIGS. 6A-6D show (A) uptake of adenovirus expressing PSMA or a luciferase gene as compared to muscle (control); (B) target to background ratio of PSMA relative to luciferase and muscle; (C) PSMA imaging using $^{18}$F-DCFBC as a probe at 60 min post injection; and (D) PSMA imaging using $^{18}$F-DCFBC as a probe at 4 hr post injection. Mice were implanted with matrigel suspensions of cells expressing either PSMA (left) or a negative control gene (luciferase, right) in the upper flanks;

FIGS. 7A-7B show monitoring of hepatic infection and transgene expression by imaging PSMA in a murine model: athymic nude mice were administered adenovirus expressing PSMA or a luciferase (negative control) gene intravenously and specific uptake was observed in the liver of animals by (A) optical and (B) SPECT imaging (obtained at 15 min post-injection of radiotracer);

FIGS. 8A-8E show an embodiment of a non-viral expression system for PSMA: (A) basic expression vector using the promoter for rat progression elevated gene-3 (PEG-Prom); (B) clinically compatible version of vector (A) equipped with CpG-free vector backbone and CpG-free PSMA cDNA; (C) episomal amplisome vector: GAL4, yeast Gal4 DNA binding protein; VP16; transcriptional enhancer from CMV; 5×UAS (5 repetitions of the upstream activation sequence); (D) schematic diagram of PSMA: CD, cytoplasmic domain; TM, transmembrane domain; ED, extracellular domain; and (E) various truncations of PSMA: FL, full length; W2G, point mutation at the second amino acid from tryptophan to glycine; C-625, truncations that lacks C-terminal part of the gene from amino acid 625; N-11, lacks N-terminal 11 amino acids;

FIGS. 9A-9B show that PSMA was expressed on the cell surface of the transfected cells: (A) FACS analyses of transfected cells using fluorescent labeled PSMA-targeted compound (YC-VIII-46); and (B) immunofluorescent analyses of transfected cells using anti-PSMA antibody;

FIG. 10 shows an in vitro radio uptake assay using MDA-MB-231 cell lines transiently transfected with the basic non-viral vector with full-length and truncations of PSMA;

FIG. 11 shows a map of a representative CpG-free-PEG-PSMA vector. This clinically compatible vector contains CpG-free PSMA cDNA, a CpG-free neo$^r$ selection marker, and a CpG-free S/MAR sequence; and FIG. 12 shows a representative cDNA sequence of a CpG-free PSMA gene

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Molecular-genetic imaging is the visualization, characterization, and measurement of biological processes at the molecular and cellular levels by using reporter gene/reporter probe systems. The prostate-specific membrane antigen (PSMA) is a human transmembrane protein that possesses many properties that are desirable as a reporter for an imaging system. PSMA is internalized upon the binding of certain ligands (Liu et al., 1998), providing a mechanism to accumulate PSMA-targeting agents within cells. The expression of PSMA is limited to the prostate, the proximal tubules of the kidney, and the brain (Rajasekaran et al., 2005). Alternative processing results in both cell surface and cytoplasmic isoforms, the latter of which is primarily expressed in the healthy prostate (Mlcochova et al., 2009). PSMA expression is low and isolated in healthy tissues, allowing imaging at high sensitivity and specificity for metastatic prostate tumors that overexpress the cell surface isoform (Afshar-Oromieh et al., 2013; Barrett et al., 2013; Cho et al., 2012). There are several PSMA-binding ligands that have been developed for the delivery of imaging and therapeutic agents for prostate cancer, including low-molecular-weight nuclear, fluorescent, and multi-modality imaging probes (Chen et al., 2009; Banerjee et al., 2011). This combination of tissue-restricted expression, human biocompatibility, available probe diversity, and proven clinical utility are some of the advantages of using PSMA as an imaging reporter. The presently disclosed subject matter provides a PSMA-based gene reporter/probe system that can be generalized for a variety of cell and tissue types.

I. PSMA Reporter Gene Constructs and Kits

In some embodiments, the presently disclosed subject matter provides a reporter gene construct comprising a PSMA gene. The PSMA gene may be from a variety of organisms, although in preferred embodiments, the gene will be a human gene (e.g., GenBank Accession No. DD461260 or NG_029170) and the PSMA protein expressed from the gene will be a human protein (e.g., GenBank Accession No. NP_004467). In some embodiments, the PSMA gene will have substantial percent identity to the sequence identified as GenBank Accession No. DD461260 NG_029170 and the PSMA protein will have substantial percent identity to the sequence identified as GenBank Accession No. NP_004467.

The term "percent identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences may be performed using the Clustal method of alignment (Higgins and Sharp (1989) *CABIOS.* 5:151-153) with the default parameters, including default parameters for pairwise alignments.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al. (1990) *J. Mol. Biol.* 215:403-410, and DNASTAR (DNASTAR, Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

It is well understood by one skilled in the art that many levels of sequence identity are useful in identifying genes and proteins for use in the presently disclosed subject matter, for example wherein genes and proteins from a different species but have the same or similar function or activity. The term "substantial identity" or "substantial percent identity" in its various grammatical forms comprises a sequence that has a desired percent identity, for example, at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% compared to a reference sequence using one of the alignment programs described using standard parameters.

The term "imaging reporter", as used herein, refers to a protein that, in combination with an imaging probe, can be used to mark cells, intracellular organelles, and the like. Examples of reporter systems include reporters that encode β-galactosidase, chloramphenicol acetyltransferase, luciferase, and green fluorescent protein (GFP). In some embodiments, the imaging reporter may act as both an imaging probe to visualize the target molecule, as well as a therapeutic agent, such as to inhibit a disease process, for example.

The term "reporter gene construct", as used herein, refers to a vector comprising the gene encoding for the imaging reporter. The reporter gene construct can contain a number of components, including, but not limited to one or more of the following: an origin of replication; a selectable marker gene; one or more expression control elements, such as a transcriptional control element (e.g., a promoter, an enhancer, a terminator), and/or one or more translation signals; and a signal sequence or leader sequence for targeting to the secretory pathway in a selected host cell. In some embodiments, the presently disclosed construct comprises all or part of a PSMA gene.

The term "promoter" or "transcriptional promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." In some embodiments, the promoter is tumor-specific, such as the promoter from a minimal promoter region of progression elevated gene-3 (Peg-3), which allows cancer-selective expression. It is further recognized that since in most cases the exact boundaries of regulatory sequences have not been completely defined, DNA fragments of different lengths may have identical promoter activity.

A coding sequence is "under the control" of transcriptional and translational control sequences in a cell when RNA polymerase transcribes the coding sequence into mRNA, which is then spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

In some embodiments, the reporter gene construct is based on a viral vector, such as a retroviral vector including a lentiviral vector, an adenoviral vector, an adeno-associated viral vector, and the like. In some embodiments, the reporter gene construct is based on an adenoviral vector. Advantages of adenoviral vectors include, but are not limited to, that they are a means to transfer equal amounts of transgene reporters, the adenovirus genome is maintained episomally and is not influenced by integration site or copy number, and adenoviruses have been applied successfully in imaging reporter gene comparisons (Gil et al., 2012; Min et al., 2003; Miyagawa et al., 2005).

In some embodiments, the presently disclosed subject matter provides an adenoviral reporter gene construct comprising a prostate-specific membrane antigen (PSMA) gene operably linked to a cytomegalovirus immediate-early gene (CMV) promoter. The CMV promoter induces high-level constitutive expression in a variety of mammalian cell lines.

In some embodiments, the presently disclosed subject matter provides a non-viral, episomal reporter gene construct. In general, in eukaryotes, episomes are closed circular DNA molecules that are replicated in the nucleus and remain physically separate from host cell chromosomes. In other embodiments, the presently disclosed subject matter provides a non-viral, episomal reporter gene construct comprising a prostate-specific membrane antigen (PSMA) gene operably linked to a PEG-Promoter, a tumor-specific promoter from a minimal promoter region of progression elevated gene-3 (Peg-3), which allows cancer-selective expression of PSMA.

In some embodiments, the non-viral, episomal reporter gene construct further comprises a Gal4-VP16 and Upstream Activation Sequence (UAS) transcriptional amplification system. In this system, the Gal4-VP16 component, a fusion protein of yeast transcriptional activator protein Gal4 and herpes simplex virus VP16, acts as an activator and the UAS component acts as an enhancer to which Gal4 specifically binds to activate gene transcription. In other embodiments, each UAS is 17 base pairs long, roughly palindromic, and in the form of CGG-N11-CCG. In other embodiments, the UAS is 5'-(T/C)GGAGTACTGTCCTCCG-3' (SEQ ID NO: 1). Multiple copies of the UAS can be inserted onto one construct, such as 2, 3, 4, 5, 6, 7, 8, 9, 10, or more. These copies may be separated by other nucleotides. In further embodiments, the transcriptional amplification system comprises five copies of the UAS. In still further embodiments, the five copies of the UAS has the sequence:

(SEQ ID NO: 2)
CGGAGTACTGTCCTCCGAGCGGAGTACTGTCCTCCGAGCGGAGTACTGTC
CTCCGAGCGGAGTACTGTCCTCCGAGCGGAGTACTGTCCTCCGAG.

In some embodiments, the non-viral, episomal reporter gene construct further comprises the EBNA-1 (Epstein-Barr nuclear antigen 1) gene, which encodes a viral protein associated with the Epstein-Barr virus, for prolonged action in transfected cells. In other embodiments, the non-viral, episomal gene construct further comprises OriP, a viral origin of plasmid replication.

In some embodiments, the PSMA gene comprises the coding sequence of the full-length PSMA protein. In other embodiments, the PSMA gene is truncated at the 5' end of the coding sequence of the PSMA protein. It has been found that N-terminal truncations of the PSMA protein, such as truncation of the first 11 amino acids, still allows the N-terminally modified PSMA to successfully localize to the cell membrane and centrosome. In still other embodiments, the truncation results in a mutated PSMA protein that is lacking the first 11 amino acids of the wild-type PSMA protein. In addition, substitution of the second amino acid in the PSMA protein from glycine to tryptophan also allows the modified PSMA protein to localize correctly. In further embodiments, the PSMA protein is mutated such that its second amino acid is glycine instead of tryptophan. In still further embodiments, the PSMA gene is mutated such that the construct expresses a mutated PSMA protein that has glycine as a second amino acid instead of tryptophan.

As used herein, the term "mutation" or "mutated" is used herein to refer to an alteration in a polynucleotide sequence, which results in an altered gene product or protein. A mutation according to the presently disclosed subject matter can involve substitution, insertion or deletion. A polynucleotide or protein in which a mutation has occurred is called a "mutant". Mutation may be introduced to one or both strands of a double-stranded polynucleotide. The strand of a double-stranded polynucleotide in which a mutation has occurred is referred to as a "mutant strand"; the strand with no mutation introduced is called a "non-mutant strand". The term "mutagenesis" according to the invention refers to the introduction of mutations into a polynucleotide sequence. The term "wild-type" as used herein refers to the normal, non-mutated version of a gene or protein.

Previous efforts have shown that PSMA expression has not significantly altered cellular phenotype in vitro in multiple mammalian cell types. In still further embodiments, functional modifications that alter PSMA enzymatic activity, ligand binding ability, cellular internalization, and the like are employed, for example in cases of negative effects of transgene expression (Anilkumar et al., 2003; Rajasekaran et al., 2003).

In some embodiments, a CpG-free version of PSMA is used that has a modified cDNA sequence that contains no CpG sequences. This modification at the DNA level does not change the protein sequence. Therefore, the CpG-free PSMA also has substantial percent identity to the protein sequence identified as GenBank Accession No. NP 004467. Accordingly, in some embodiments, the PSMA gene is CpG-free.

In other embodiments, the reporter gene construct comprising a PSMA gene is CpG-free. In still other embodiments, a presently disclosed clinically compatible vector is equipped with CpG-free sequences. In further embodiments, a CpG-free-PEG-PSMA vector comprises a CpG-free R6K gamma origin of replication, a CpG-free polyadenylation signal, a CpG-free Neomycin/Kanamycin resistant gene, a CpG-free S/MAR sequence and a CpG-free PSMA. Using the CpG-free DNA prevents harmful immune reaction in human via Toll-like receptor 9 (Bauer et al., 2001) and using a Neomycin/Kanamycin resistant gene allows the presently disclosed vectors to be employed for clinical use (FDA, 1996).

As used herein, a "CpG site" is a region of DNA where a cytosine nucleotide occurs next to a guanine nucleotide. Cytosines in CpG sites can be methylated to form 5-methylcytosine. As used herein, the term "CpG-free" means that the gene and/or construct does not have any CpG sites.

In some embodiments, the presently disclosed subject matter provides a kit comprising a presently disclosed construct. In general, a presently disclosed kit contains some or all of the components, reagents, supplies, and the like to practice a method according to the presently disclosed subject matter. In other embodiments, the term "kit" refers to any intended article of manufacture (e.g., a package or a container) comprising a presently disclosed reporter gene construct and a set of particular instructions for practicing the methods of the presently disclosed subject matter.

II. Methods for Using PSMA as an Imaging Reporter

In some embodiments, the presently disclosed subject matter provides a method for using prostate-specific membrane antigen (PSMA) as an imaging reporter, the method comprising: a) introducing a reporter gene construct comprising a PSMA gene operably linked to a transcriptional promoter to a cell; b) allowing the cell to express PSMA protein; c) adding an imaging probe that can detect the PSMA protein to the cell; and d) imaging the imaging probe, thereby detecting the PSMA protein. The presently disclosed constructs can be used in the presently disclosed methods and are described in detail hereinabove.

In some embodiments, the reporter gene construct is a viral reporter gene construct. In other embodiments, the viral reporter gene construct is an adenoviral reporter gene construct. In still other embodiments, the reporter gene construct is a non-viral, episomal reporter gene construct.

In some embodiments, the transcriptional promoter is a constitutive promoter. In other embodiments, the constitutive promoter is the cytomegalovirus immediate-early gene (CMV) promoter. In still other embodiments, the transcriptional promoter is the PEG-Promoter.

In some embodiments, the non-viral, episomal reporter gene construct further comprises a Gal4-VP16 and Upstream Activation Sequence (UAS) transcriptional amplification system. In other embodiments, the transcriptional amplification system comprises five copies of the UAS.

In some embodiments, the non-viral, episomal reporter gene construct further comprises the EBNA-1 gene. In other embodiments, the non-viral, episomal reporter gene construct further comprises OriP.

In some embodiments, the PSMA gene comprises the coding sequence of the full-length PSMA protein. In other embodiments, the PSMA gene is truncated at the 5' end of the coding sequence of the PSMA protein. In still other embodiments, the truncation results in a mutated PSMA protein that is lacking the first 11 amino acids of the wild-type PSMA protein. In further embodiments, the PSMA protein is mutated such that its second amino acid is glycine instead of tryptophan.

In some embodiments, the PSMA gene is CpG-free. In other embodiments, the reporter gene construct comprising a PSMA gene is CpG-free. In still other embodiments, the reporter gene construct comprising a PSMA gene further comprises a neomycin or kanamycin resistant gene.

In some embodiments, the presently disclosed method comprises introducing a reporter gene construct comprising a PSMA gene operably linked to a transcriptional promoter to a cell. Introducing the reporter gene construct to a cell may be performed using electroporation, DEAE Dextran transfection, calcium phosphate transfection, cationic liposome fusion, protoplast fusion, creation of an in vivo electric field, DNA-coated microprojectile bombardment, injection with recombinant replication-defective viruses, homologous recombination, in vivo gene therapy, ex vivo gene therapy, viral vectors, naked DNA transfer, and any other method that will allow the reporter gene construct to enter the cell.

In some embodiments, the cell is found in a subject, in which case introducing the reporter gene construct to a cell may also occur by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

In those embodiments where the cell is found in a subject, the cell is desirably a human cell, although it is to be understood that the methods described herein are effective with respect to the cells of all vertebrate species, which are intended to be included in the term "subject." Suitable animal cells include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal cell may be a transgenic animal cell. In some embodiments, the cell is a human cell including, but not limited to, fetal, neonatal, infant, juvenile, and adult human cells. Further, a "cell" can include a diseased cell, such as a cancer cell. In other embodiments, the subject is human.

In some embodiments, after introducing a reporter gene construct comprising a PSMA gene operably linked to a transcriptional promoter of a cell, the methods comprise allowing the cell to express the PSMA protein. By "express" or "expressing", it is meant the process by which information from a gene is used in the synthesis of a functional gene product, such as a protein.

In some embodiments, an imaging probe is then added to detect the PSMA protein. By "detect" or "detecting", it is meant that the imaging probe binds, is cleaved by, or in some way interacts with the expressed PSMA protein. A variety of imaging probes can be used, although in a preferred embodiment, the imaging probe allows for sensitive, non-invasive imaging. In another preferred embodiment, the imaging probe is compatible with human use (non-immunogenic).

In some embodiments, PSMA-binding ligands can be used as imaging probes, such as low-molecular-weight nuclear, fluorescent, and multi-modality imaging probes. In other embodiments, the imaging probe is chosen depending on the pharmacokinetics and sensitivity required for a particular indication. In still other embodiments, a high-affinity imaging probe is used that does not serve as a substrate. In still further embodiments, the imaging probe may bind the active site of PSMA electrostatically, treating it essentially as a receptor ("receptor" probe). In further embodiments, the imaging probe may be a PSMA inhibitor.

Accordingly, in some embodiments, the imaging probe detects the PSMA protein by binding to the active site of the PSMA protein. In other embodiments, (aminostyryl)pyridinium (ASP) dyes are used as imaging probes. In still other embodiments, the imaging probe is 2-(3-{1-carboxy-5-[(6-[$^{18}$F]fluoro-pyridine-3-carbonyl)-amino]-pentyl}-ureido)-pentanedioic acid (DCFPyL) or N—[N—[(S)-1,3-dicarboxypropyl]carbamoyl]-4-[$^{18}$F]fluorobenzyl-L-cysteine (DCFBC).

An advantage of using PSMA as an imaging reporter is that it possesses enzymatic activity. Therefore, in some embodiments, the imaging probe may be an "enzymatic" probe, the cleavage products of which can be fluorescent and/or radioactive. In other embodiments, the cleavage products of the probe intercalate within the target cell membrane. In still other embodiments, an enzymatic imaging probe is used for the detection of cellular events. Accordingly, in some embodiments, the presently disclosed methods further comprise the cleavage of the imaging probe by the PSMA protein. In other embodiments, cleavage of the imaging probe results in at least one cleavage product that is fluorescent and/or radioactive.

In some embodiments, after adding the imaging probe, the presently disclosed methods comprise imaging the probe, thereby detecting the PSMA protein. Molecular imaging can be performed with a range of instruments, most of which utilize a specific region of the electromagnetic spectrum. These imaging modalities include, but are not limited to, magnetic resonance imaging (MRI), x-ray computed tomography (CT), positron emission tomography (PET), single photon emission computed tomography (SPECT), and optical (bioluminescence and fluorescence imaging). In other embodiments, imaging the PSMA protein occurs by at least one method selected from the group consisting of near-infrared (NIR) optical tomography, positron emission tomography (PET), and single photon emission computed tomography (SPECT).

In some embodiments, the PSMA protein is detected on the surface of the cell. In other embodiments, the PSMA protein is detected inside the cell. In still other embodiments, the imaging probe is imaged on the cell surface. In further embodiments, the imaging probe is imaged inside the cell. The term "surface of the cell" or "cell surface" as used herein means the outer surface of the cell, including the cell or plasma membrane. In further embodiments, the PSMA protein or imaging probe may intercalate within the cell membrane, which means herein that the PSMA protein or imaging probe is still on the cell surface.

In some embodiments, the presently disclosed subject matter enables non-invasive imaging of in vivo gene expression, such as for the study of signal transduction pathways and protein interaction networks, the study of the underlying physiology or pathophysiology of disease, such as cancer and neurodegenerative diseases, help in developing new, selective drugs for various diseases, and the like.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Genetic reporters provide a non-invasive method to monitor and evaluate a population of cells. The ideal properties of a gene reporter-probe system include biocompatibility, lack of immunogenicity, low background expression or signal, and high sensitivity of detection. The prostate-specific membrane antigen (PSMA) is an attractive candidate for a genetic reporter as it is a human transmembrane protein with a very selective expression pattern and there are several PSMA imaging agents available for clinical and pre-clinical applications. The present studies evaluated the use of PSMA as a genetic imaging reporter by comparison to two clinically established reporters, the mutant herpes simplex virus type I thymidine kinase and the human sodium-iodide symporter. Adenoviruses expressing each reporter were constructed and validated in vitro for expression and function. To compare PSMA to existing imaging reporters, a bilateral matrigel suspension model was established with nude mice bearing cells equally infected with each reporter or control adenovirus. Dynamic PET scans were performed and time-activity curves were generated for each reporter-probe pair. A comparison of peak target-to-background ratios revealed that PSMA offered the highest ratio relative to the control matrigel suspension as well as muscle. Further, PSMA was applied as an imaging reporter to monitor adenoviral liver transduction with both nuclear and optical imaging probes.

Materials and Methods

Chemicals and primers were purchased from Sigma-Aldrich (St. Louis, Mo.). Cell culture reagents were purchased from Mediatech, Inc. (Manassas, Va.), Gemini Bio-Products (Woodland, Calif.), and Invitrogen (Carlsbad, Calif.). Restriction enzymes and DNA modifying enzymes were purchased from New England Biolabs (Ipswich, Mass.). Plasmid and gel purification components were purchased from Qiagen, Inc. (Valencia, Calif.) or Sigma-Aldrich. Transfection reagent was purchased from Invitrogen. Adenovirus purification kits were purchased from Puresyn, Inc. (Malvern, Pa.). [$^3$H]Gancyclovir ([$^3$H]GCV) was purchased from Moravek Biochemicals (Brea, Calif.). [$^{125}$I]NaI was purchased from MP Biomedicals (Solon, Ohio). The J591 antibody was kindly provided by Dr. Neil Bander (Weill Cornell Medical College, NY).

Cell Culture.

Cell culture media contained 50 μg/mL gentamycin and 5 μg/mL ciprofloxacin to prevent bacterial contamination.

HCT116 cells were obtained from Dr. Bert Vogelstein (Johns Hopkins University, MD) and grown in McCoy's 5A supplemented with 10% FBS. DPL cells were generated in the lab of Dr. Ronald Rodriguez and grown in DMEM supplemented with 10% FBS (Hoti et al., 2007). PC3-CAR cells were obtained from Dr. J. T. Hsieh (University of Texas Southwestern Medical School, TX) and grown in RPMI 1640 medium supplemented with 10% FBS and 300 µg/mL G418.

Cloning of Adenoviral Vectors.

Viruses were generated using the AdEasy vector system (Luo et al., 2007). PSMA was sub-cloned from pDonor-CMV-PSMA into pAd-Track-CMV using BglII and NotI. hNIS was sub-cloned from pDonor-CMV-hNIS into pAd-Track-CMV using BglII and NotI. The CMV promoter was sub-cloned by PCR using primers 5'-CMV (ACGAA-GATCTTAATAGTAATCAATTACGGGG) (SEQ ID NO: 3) and 3'-CMV (TCCGGAATTCCTAGCG-GATCTGACGGTTCAC) (SEQ ID NO: 4) upstream of sr39tk-GFP in the shuttle plasmid pGal-mNLS-sr39tk-EGFP using BglII and EcoRI restriction sites. The expression cassette from pCMV-mNLS-sr39tk-EGFP was then cloned into RpSWC1 using NotI and SalI restriction sites. The resulting plasmids, pAd-Track-CMV-PSMA, pAd-Track-CMV-NIS, or RpS-CMV-mNLS-sr39tk-EGFP were recombined with pAdEasy-1 vector in BJ5183 *Escherichia coli* and selected for kanamycin resistance. Each resulting viral genome was linearized with Pac I and transfected into DPL cells for virus production. The resulting adenoviruses were column purified using Adenopure adenovirus purification kit and titered in HEK293 cells by GFP and Hexon staining with Adeno-X rapid titer kit (Clonetech, Mountain View, Calif.) 36 hours post-infection.

Preparation of J591 Antibody Conjugated to IRDye 800CW.

The J591 antibody was labeled by using IRDye® 800CW NHS Ester (LI-COR, Lincoln, Nebr.). Briefly, 20 µL of 3 mM IRDye® 800CW NHS Ester (~10 molar fold excess in DMSO) were added to 200 µL of J591 antibody (5 mg/mL in PBS) and kept 1 h at ambient temperature. The unreacted dye was removed by passing through Zeba desalting column (Pierce, Thermo Fisher Scientific, Rockford, Ill.). The conjugation of dye was confirmed by measuring Absorbance at 280 and 750 nm and by SDS-PAGE.

Western Blot.

Cells were washed with 1×PBS and re-suspended in RIPA lysis buffer supplemented with protease inhibitor cocktail (Roche, Indianapolis, Ind.) and incubated on ice for 30 minutes and then centrifuged for 10 minutes at 4° C. Total protein concentration was measured using the Micro BCA Protein Assay Kit (Thermo Scientific, Rockford, Ill.) according to the manufacturer's protocol. Equal amounts of proteins were separated by SDS-PAGE and transferred to PVDF membrane, blocked with 5% nonfat dry milk in PBS for 1 hour at room temperature, and then incubated with primary antibody (mouse monoclonal anti-hNIS from ABCAM [SPM186], mouse monoclonal anti-PSMA J591, rabbit polyclonal anti-HSV TK obtained from Dr. William Summers (Yale University, New Haven, Conn.) overnight at 4° C. The membrane was then probed with anti-mouse IR800 conjugated secondary antibody or anti-rabbit IR680 conjugated secondary antibody for 1 hour and scanned on the Odyssey Infrared Imager (LI-COR, Lincoln, Nebr.) using the manufacturer's protocol.

Fluorescent Cellular Immunoassay.

Control cells or cells infected with reporter virus were plated on 96-well plates. When 90% confluent, cells were washed with 1×PBS and fixed with 4% paraformaldehyde for 30 minutes at room temperature. After fixation, cells were washed with 1×PBS, blocked with 1% BSA in PBS for 1 hour at room temperature, and incubated with primary antibodies described above at 37° C. for 1 hour. Cells were then probed with secondary antibody conjugated with IR800 for 1 hour and scanned on the Odyssey Infrared Imager using the manufacturer's protocol.

Cell Uptake Assays.

Cellular uptake of $^{125}$I was measured in a fashion similar to that of De la Vieja (De la Vieja et al., 2005), while HSV-SR39TK expression was measured as described by Yaghoubi et al. (2006). PSMA expression was assessed by measuring cellular uptake of the known, high-affinity PSMA targeting ligand, 2-[3-[1-carboxy-5-(4-[$^{125}$I]iodo-benzoylamino)-pentyl]-ureido]-pentanedioic acid (YC-I-27) (Chen et al., 2008). For uptake of $^{125}$I, cells were harvested in PBS using a cell scraper and placed in a FACS tube for quantification in an automated γ-counter (1282 Compugamma CS, Pharmacia/LKB Nuclear, Inc., Gaithersburg, Md.). For [$^{3}$H] GCV, the amount of radiolabeled substrate retained was quantified by scintillation counting on a Microbeta Wallac (Perkin-Elmer, Waltham, Mass.). YC-I-27 uptake was also measured using the automated γ-counter. In each case, uptake was calculated as amount of radioactivity in the cells divided by radioactivity in the media and normalized by the degree of expression of green fluorescent protein (GFP).

In Vivo Imaging.

Studies were performed according to protocols approved by the Animal Care and Use Committee at Johns Hopkins University. A matrigel suspension model was developed to enable imaging of similar numbers of cells in vivo. Four- to six-week-old athymic male nude mice (Harlan Laboratories Inc., Frederick, Md.) were used for all experiments. $4\times10^6$ infected cells were injected subcutaneously in the presence of Matrigel (BD Biosciences, Bedford, Mass.) at a 2:1 (cell:matrigel) ratio.

PET was performed for in vivo reporter comparison. 9-(4-[$^{18}$F]Fluoro-3-[hydroxymethyl]butyl)guanine (FHBG) and 2-(3-{1-carboxy-5-[(6-[$^{18}$F]fluoro-pyridine-3-carbonyl)-amino]-pentyl}-ureido)-pentanedioic acid (DCFPyL) were synthesized as previously described (Ponde et al., 2004; Chen et al., 2011). [$^{124}$I]NaI was kindly provided by Dr. Jason Lewis (Memorial Sloan-Kettering Cancer Center, NY). Athymic nude mice contralaterally implanted with reporter or control expressing matrigel suspensions in the upper flanks were used for imaging. Mice were anesthetized with 3% isoflurane in oxygen for induction and were maintained under 1.5% isoflurane in oxygen at a flow rate of 0.8 L/min. Mice were then placed in the prone position on the gantry of a GE eXplore VISTA small animal PET scanner (GE Healthcare Life Sciences, Pittsburgh, Pa.) and injected intravenously with ~7.4 MBq (200 µCi) in 200 µL of PBS of each respective radiotracer. Images were acquired as a dynamic scan of 18 five-minute frames at 250 to 700 keV for $^{18}$F and 400-700 keV for $^{124}$I. Images were reconstructed using the FORE/2D-OSEM method (1 iteration, 16 subsets) and included correction for radioactive decay, scanner dead time, and scattered radiation. After PET imaging, the mobile mouse holder was placed on the gantry of an X-SPECT (Gamma Medica-Ideas, Salem, N.H.) small animal imaging device to acquire the corresponding CT. PET and CT data were co-registered using AMIDE software (sourceforge.net).

To apply PSMA as a reporter by imaging transduced hepatocytes, near-infrared (NIR) optical and single photon emission computed tomographic (SPECT) imaging were performed. Nude mice were injected intravenously with 1×10$^7$ IU of Ad-Track-PSMA or Ad-Track-Luciferase in a 200 μL volume. Luciferase was not used for imaging in this instance but as a control gene. For NIR imaging, 24 hours after Ad-Track-PSMA or Ad-Track-Luciferase animals were administered 15 μg or 30 μg of Anti-PSMA Antibody, J591 conjugated with IR800 in 200 μL of PBS via the lateral tail vein. For SPECT animals received ~7.4 MBq (200 μCi) of the known, high-affinity PSMA targeting ligand, 2-(3-[1-carboxy-5-[(5-[$^{125}$I]iodo-pyridine-3-carbonyl)-amino]-pentyl]-ureido)-pentanedioic acid (YC-VI-11) (Chen et al., 2008) in 200 μL of PBS also at 24 hours after Ad-Track-PSMA or Ad-Track-Luciferase. Animals received inhalational anesthesia (isoflurane) through a nose cone attached to the imaging bed. NIR images were acquired 48 hours post-injection of conjugated J591 and imaged using the Pearl Impulse (LI-COR, Lincoln, Nebr.), while SPECT images were acquired after 15 minutes of radiopharmaceutical uptake using the X-SPECT. For SPECT scans, mice were scanned over 180° in 5.5°, 30 second increments. SPECT images were co-registered with CT. For each modality, images for Ad-Track-PSMA or Ad-Track-Luciferase were acquired at the same parameter settings and scaled to the same maximum values.

Statistical Analysis.

Statistical analysis was performed using GraphPad Prism software (GraphPad Software, Inc., La Jolla, Calif.). An unpaired, 2-tailed t test was used and P-values <0.05 were considered significant.

Radiochemical Syntheses.

Radiotracers used for PET, i.e., FHBG, [$^{124}$I]NaI, DCFPyL and N—[N—[(S)-1,3-dicarboxypropyl]carbamoyl]-4-[$^{18}$F]fluorobenzyl-L-cysteine (DCFBC) (Cho et al., 2012), were synthesized at specific activities of 340±14 Ci/mmol (12.6±0.5 GBq/μmol), with no carrier added, 1,180±665 Ci/mmol (43.7±24.6 GBq/μmol) and 21,233±14, 651 Ci/mmol (786±542 GBq/μmol), respectively. Despite the significant difference in specific activity between DCFPyL and DCFBC, similar results were obtained on imaging (see herein below).

Adenoviral Reporter Comparison Model

The presently disclosed subject matter provides the development of PSMA as an imaging reporter and the comparison of PSMA to established imaging reporters. Three putative reporter genes, PSMA, mutant herpes simplex virus thymidine kinase (HSV-sr39tk), and human sodium iodide symporter (hNIS), were sub-cloned downstream of a cytomegalovirus (CMV) promoter in the E1 region of non-replicating serotype 5 adenoviruses (Table 1). HSV-sr39tk and hNIS have been applied clinically (Barton et al., 2008; Yaghoubi et al., 2001). Each viral construct also expressed GFP for fluorescence detection of viral infection and titering. Two cell line models, HCT116 colon cancer cells and PC3 prostate cancer cells engineered to express stably the coxsackie adenovirus receptor (PC3-CAR), were applied to viral reporter studies. The expression of each reporter was validated by western blot analysis of infected HCT116 cells (multiplicity of infection, MOI=1) 48 hours after infection.

Figure 1A:
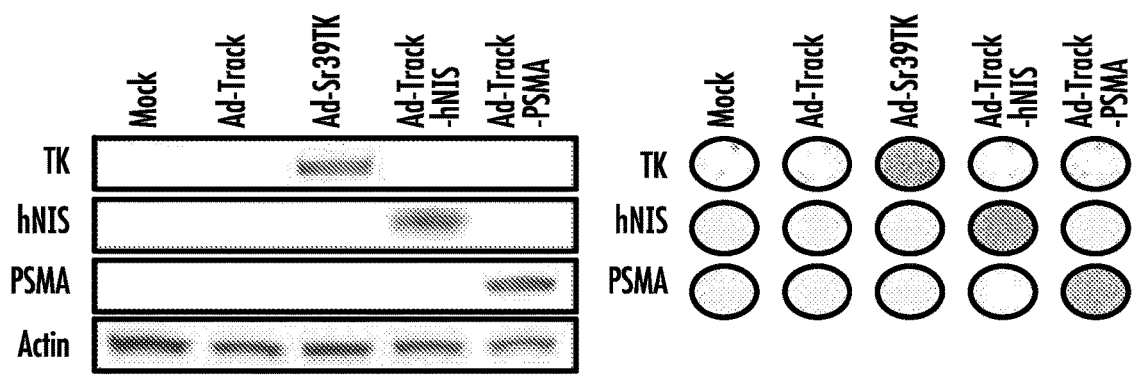

Each reporter was detected at the appropriate molecular weight in infected cells and no endogenous expression was visible under mock-infected or Ad-Track (GFP) infected control conditions (FIG. 1A). In addition, specific transgene delivery and expression were detected by a cell-based fluorescent immunoassay (FIG. 1A). Specifically, PC3-CAR cells were equally infected with each reporter adenovirus (MOI=500) and fixed 48 hours after infection. Reporter protein expression was detected by primary antibody incubation followed by fluorescent secondary antibody staining and detection on a fluorescent plate reader. The results confirm homogeneous transgene expression and specificity by immunodetection.

TABLE 1

Description of reporter adenoviruses and respective imaging modalities used for detection of reporter genes.

| Virus | Reporter Gene | Imaging Modalities |
|---|---|---|
| Ad-Track-PSMA | prostate-specific membrane antigen | Optical, PET, SPECT |
| Ad-Track-hNIS | human sodium iodide symporter | PET, SPECT |
| Ad-HSV-sr39tk | herpes simplex virus mutant thymidine kinase | PET |

In Vitro Functionality of Adenoviral Reporter Vectors

Figure 1B:
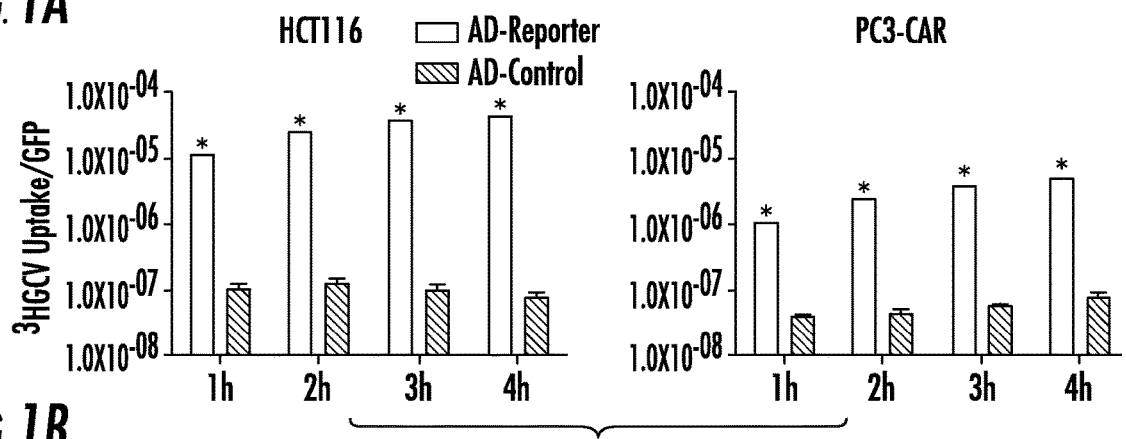
Figure 1C:
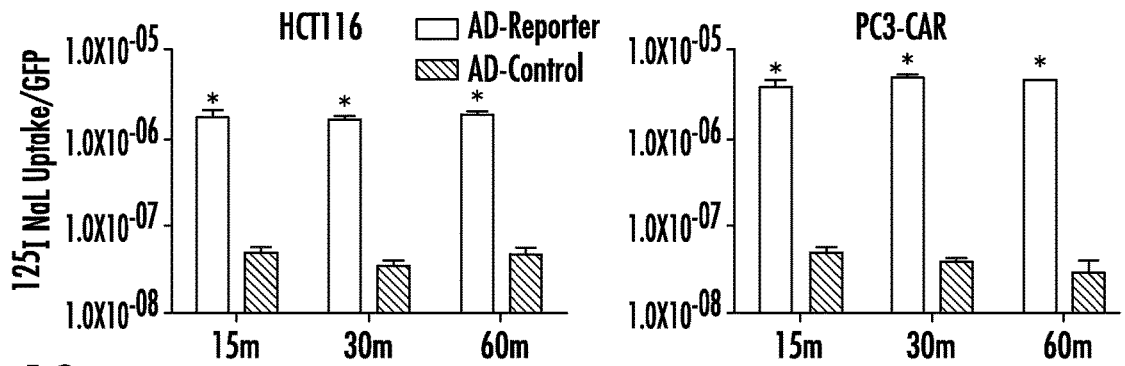
Figure 1D:
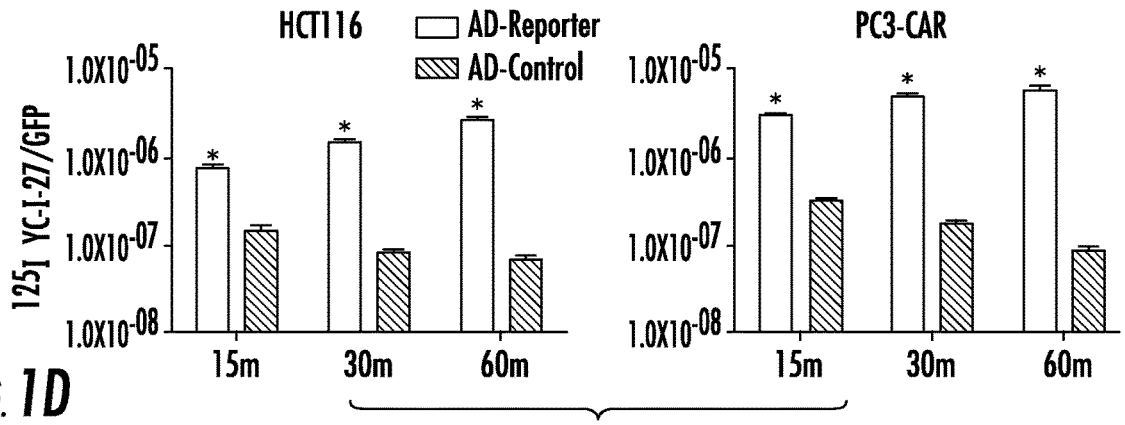

Functional assays for each reporter were analyzed using HCT116 and PC3-CAR cell lines by [$^3$H]GCV uptake, $^{125}$I uptake, and YC-I-27 binding. Cells were infected with each reporter adenovirus. After 48 hours, the level of adenovirus infection was quantified by GFP fluorescence and the level of imaging reporter activity was quantified by functional binding and/or uptake of radiolabeled probes. Specific assay conditions were applied for each reporter gene due to the different mechanisms of reporter probe binding and/or uptake. Conditions were based on previously established assay conditions from previous efforts and in the literature (De la Vieja, 2005; Yaghoubi et al., 2006). For GCV uptake, a prolonged washout period was not performed and as a result does not differentiate between phosphorylated GCV and unphosphorylated GCV that is associated with the cells at time of harvest. YC-I-27 uptake in PSMA infected cells proved more time dependent than the corresponding radiotracers were for NIS or HSV-sr39tk. Without wishing to be bound to any one particular theory, it is believed that this may be due to the mechanism of sequestration, whereby [$^{124}$I]NaI and GCV were able to diffuse passively or are transported into cells where they are trapped, whereas YC-I-27 can only enter the cell via binding and internalization of PSMA at a 1:1 stoichometry. Despite those caveats, in all cases specific and significant uptake was observed in cells infected with reporter adenovirus resulting in a signal-to-noise ratio of at least 10- to 20-fold relative to control adenovirus (FIGS. 1B-1D).

In Vivo Comparison of Adenoviral Imaging Reporters

To compare reporter-probe systems in vivo, a matrigel suspension model was developed (FIG. 2). In this model, PC3-CAR cells were infected in vitro with equal MOI (multiplicity of infection) of a PET imaging reporter or control adenovirus (AdTrack-Luciferase) and then each population of infected cells was separately mixed with matrigel and implanted contralaterally into the upper flanks of a nude mouse (24 hours post-infection). Luciferase was not used for imaging but as a control gene. Twenty-four hours after implantation, in vivo GFP imaging was performed to ensure that a similar level of control and reporter-infected cells remained at the sites of implantation. The contralateral cells masses were generally within 30% as measured by GFP imaging in vivo (FIG. 3).

The next day (48 hours after implantation), animals were subjected to a dynamic PET study whereby ~7.4 MBq (200 µCi) of each respective radiotracer was administered intravenously and cellular uptake was quantified for a duration of 90 minutes. FHBG was applied for HSV-sr39tk imaging, [$^{124}$I]NaI for hNIS imaging, and DCFPyL was applied for imaging of PSMA (Yaghoubi et al., 2001; Chen et al., 2011; Dingli et al., 2006). This model was used for comparing the reporter-probe systems for at least three reasons: (1) in vitro infection allowed equal transgene delivery of reporters and direct evaluation of implantation by GFP imaging; (2) the application of a relatively small number of cells and the short duration of the experiment minimized the influence of biologic events, such as cell growth or substantial development of tumor vasculature, on imaging reporter activity; and (3) the reporter virus was compared to a control virus within the same animal, providing an additional control to obviate animal-to-animal variation.

Figure 4A:
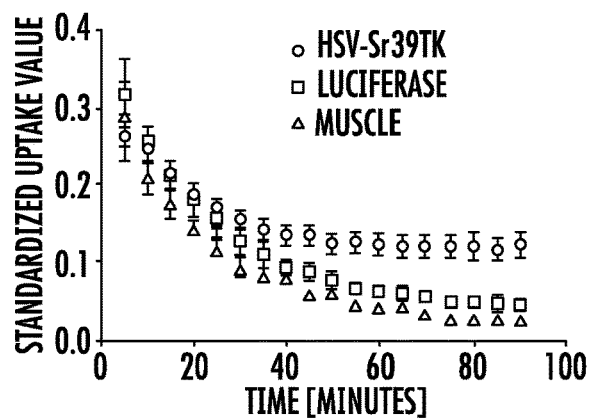
Figure 4B:
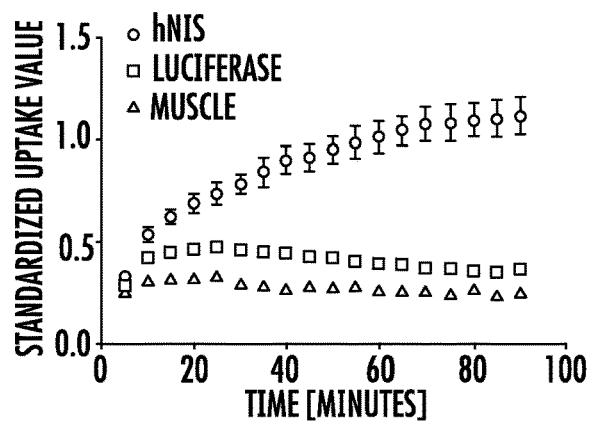
Figure 4C:
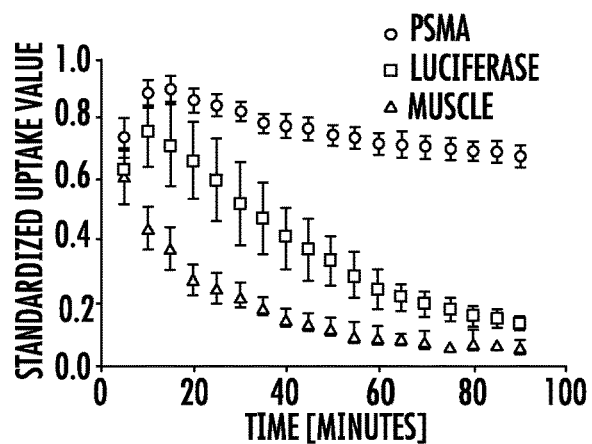
Figure 4D:
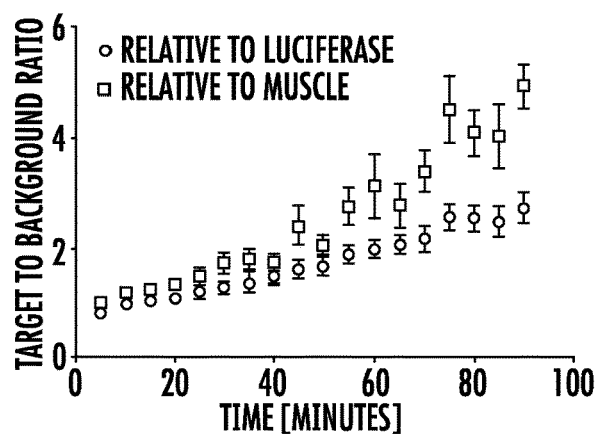
Figure 4E:
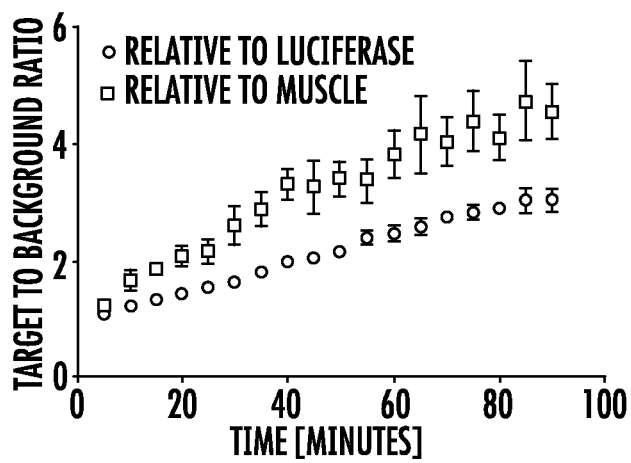
Figure 4F:
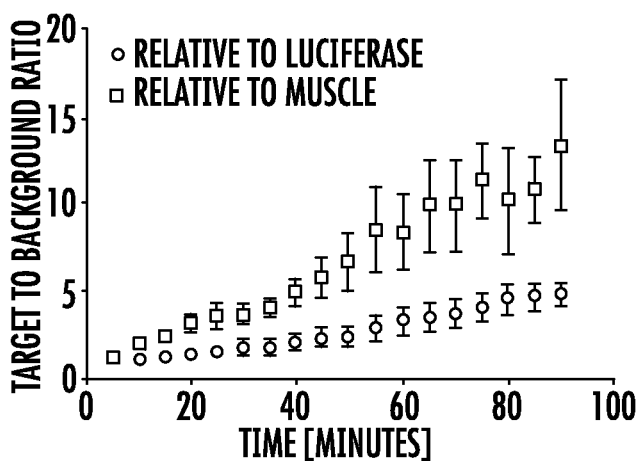
Figure 4G:
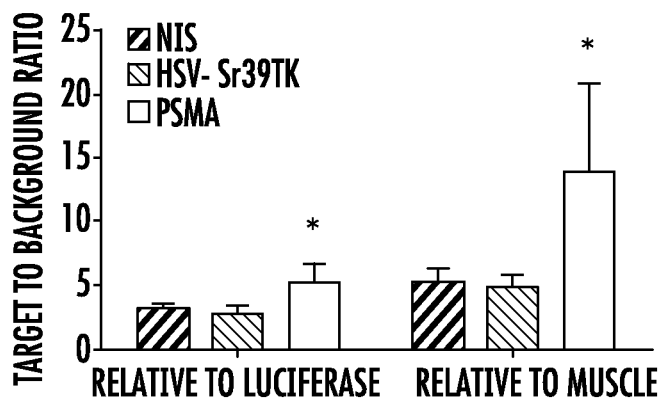

Kinetic uptake of each imaging reporter in target and control tissue was represented as a standardized uptake value (SUV) (FIGS. 4A-4C) or SUV relative to control tissue (FIGS. 4D-4F). For the HSV-sr39tk reporter, high initial uptake was observed in all tissues followed by rapid clearance from cells (FIG. 4A). HSV-sr39tk-specific sequestration of the radiotracer was observed after 30 to 40 minutes. The initial and rapid uptake of FHBG was attributed to diffusion of the compound into the cells where the unphosphorylated radiotracer diffuses out of the cells while phosphorylated tracer was retained. A peak target-to-background ratio of 2.81±0.27 relative to control cells and 4.99±0.38 relative to muscle was observed (FIG. 4G). The signal accumulation in hNIS expressing cells occurred quickly and reached a plateau roughly 80 to 90 minutes after injection (FIG. 4B). No significant uptake was observed in control tissue. A peak target-to-background ratio of 3.13±0.20 relative to control cells and 4.96±0.65 relative to muscle was observed (FIG. 4G). Despite differences in the mechanism of reporter probe accumulation, both the maximum signal-to-background ratios and the maximum percentage injected dose per cubic centimeter of tissue (% ID/cc) values of these two imaging reporters were similar. This supports the utility of the matrigel suspension model as a means to compare PSMA to the existing reporter-probe systems.

Kinetics of the PSMA imaging reporter using DCFPyL displayed rapid probe uptake with the signal peaking 15 minutes post-injection, followed by a plateau shortly thereafter (FIG. 4C). Clearance from control tissue occurred more slowly for DCFPyL than for the radioligands used for the hNIS and HSV-sr39tk systems. A peak target-to-background ratio of 5.19±0.78 relative to control cells and 13.80±3.52 relative to muscle were observed (FIG. 4G). The maximum intensity projection images, cropped above the liver and below the thyroid for each reporter-probe system, demonstrate the specific uptake in the reporter expressing cells when compared to the muscle or to control matrigel suspension (FIG. 5A). The target-to-background profiles revealed that a signal-to-noise ratio of greater than two (relative to muscle) could be detected after 45 minutes for HSV-sr39tk, 20 minutes for hNIS, and 10 minutes for PSMA (FIGS. 4D-4F).

Maximum signal-to-noise ratios were observed at 90 minutes, with the PSMA system having the highest ratio relative both to the luciferase matrigel suspension and the muscle (FIG. 4G). Uncropped images from each scan highlight the differences in efficiency of the reporter to sequester its cognate probe and demonstrate background due to natural expression of reporter genes or probe metabolism (FIG. 5B). High gastrointestinal uptake was observed in the HSV-sr39tk system, which has previously been attributed to probe metabolism (Tjuvajev et al., 2002). Background signal from the stomach and thyroid were observed in the hNIS system due to natural expression of hNIS in these tissues. For PSMA, kidney uptake was observed in part due to renal clearance as well as PSMA expression in the proximal tubules (Bacich et al., 2001). The PSMA reporter-probe system was also evaluated using DCFBC, which has been administered to patients (Cho et al., 2012; Mease et al., 2008). Results from DCFBC were similar to results obtained with DCFPyL, with the exception of a slower clearance from the control matrigel suspension (FIG. 6).

Application of the Adenoviral PSMA Reporter System

It has been previously reported in rodent models that adenoviral vectors administered via systemic injection will result in hepatocyte infection and transgene expression (Johnson et al., 2006). Optical imaging of mouse livers was performed 72 hours post-infection and 48 hours post-administration of 15 or 30 µg of J591-IR800 (FIG. 7A). Regions of interest were drawn around the liver and a signal-to-noise ratio of approximately 3:1 was observed for the PSMA imaging reporter relative to control adenovirus. This model was also applied to PSMA-specific imaging with SPECT using YC-VI-11 (Chen et al., 2008), with similar results, where a signal-to-noise ratio of approximately 2:1 was observed 15 min post-administration of radiotracer (FIG. 7B). Similar levels of radioactivity were observed in the liver at 4 h post-injection. Collectively, these results reveal PSMA as a sensitive and specific imaging reporter that can be applied to multiple imaging modalities.

Non-Viral PSMA Reporter System

Three non-viral vector systems were created for systemic delivery and expression of PSMA as an imaging reporter (FIGS. 8A-8C). These vectors employed PEG-Promoter, a tumor-specific promoter from a minimal promoter region of progression elevated gene-3 (Peg-3), for cancer-selective expression of PSMA.

One of the vectors comprised additional features to enhance its functionality as an imaging reporter vector (FIG. 8C). This vector had the Gal4-VP16 and UAS transcriptional amplification system to enhance the expression level of PSMA. In addition, this vector used OriP, a viral origin of plasmid replication, and EBNA-1, a viral protein associated with the Epstein-Barr virus, for prolonged action in transfected cells.

A third vector was created to comply with the clinical requirement for human application. This vector featured CpG-free sequences for reduced immunity and used the FDA-approved Neomycin resistant gene as a selection marker (FIG. 8B). This vector used a CpG-free R6K origin for plasmid replication and a CpG-free S/MAR sequence for elongated expression (FIG. 11). FIG. 12 shows a representative cDNA sequence of a CpG-free PSMA gene (SEQ ID NO:5).

Various truncations of PSMA were also created in addition to the full-length gene (FIGS. 8D-8E) to test the effect on the physiological status of the transfected cells. It was found that the full-length (FL) and two N-terminally modified PSMA (FL(W2G) and N-11) were successfully localized to the cell membrane and centrosome as examined by FACS analyses (FIG. 9A) and an immunofluorescent study (FIG. 9B), whereas the C-terminally truncated PSMA (C625 and N-11/C-625) failed to localize to the plasma membrane, indicating the importance of the C-terminal dimerization domain for its proper folding and localization.

The basic expression vectors (FIG. 8A) were tested for the ability to uptake a radio-labeled PSMA-targeted molecule ($^{125}$I-YC27). FIG. 10 shows an in vitro radio uptake assay using MDA-MB-231 cell lines transiently transfected with the basic non-viral vector with full-length and truncations of PSMA. Twenty-four hours after the transfection, cells were treated with 1 µCi of $^{125}$I-YC27, washed twice and the uptake was measured. Only full-length and N-terminally truncated PSMA were able to specifically uptake the substrate (FIG. 10).

Discussion

The presently disclosed subject matter provides PSMA, a biomarker for prostate cancer located on the cell membrane which possesses receptor, transporter and enzymatic functions, as an imaging reporter. The results demonstrate that PSMA is able to sequester imaging ligands with high affinity and with a high target-to-background ratio. Additional studies support PSMA as an imaging reporter with PET, SPECT, and optical imaging modalities.

The PSMA probes evaluated herein, as well as other probes in clinical and preclinical development, bind to the active site of PSMA on the surface of the cell. Enzymatic and transporter based reporter genes are able to amplify the signal by accumulation of probe, whereas receptor based reporters can only yield a 1:1 stoichiometry of probe to reporter gene molecule. The presently disclosed subject matter suggests that ligand binding alone is sufficient for detection and yields a higher signal-to-noise ratio with the PSMA-based reporter-probe system than the hNIS and HSV-sr39tk reporter-probe systems. In addition, after ligand binding, PSMA can internalize and the enzymatic and/or transporter properties of PSMA can be exploited for signal retention and amplification. As advances in cell engineering and gene therapies emerge, PSMA can provide a sensitive and non-immunogenic reporter by which to follow their fate in vivo, non-invasively.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Afshar-Oromieh, A.; Malcher, A.; Eder, M. et al. PET imaging with a [68Ga]gallium-labelled PSMA ligand for the diagnosis of prostate cancer: biodistribution in humans and first evaluation of tumour lesions. *Eur. J. NucL Med. Mol. I.* 2013, 40(4):486-495.

Anilkumar, G.; Rajasekaran, S. A.; Wang, S.; Hankinson, O.; Bander, N. H.; Rajasekaran, A. K. Prostate-specific membrane antigen association with filamin A modulates its internalization and NAALADase activity. *Cancer Research.* 2003, 63(10):2645-2648.

Bacich, D. J.; Pinto, J. T.; Tong, W. P.; Heston, W. D. Cloning, expression, genomic localization, and enzymatic activities of the mouse homolog of prostate-specific membrane antigen/NAALADase/folate hydrolase. *Mamm Genome.* 2001, 12(2):117-123.

Banerjee, S. R.; Pullambhatla, M.; Byun, Y. et al. Sequential SPECT and optical imaging of experimental models of prostate cancer with a dual modality inhibitor of the prostate-specific membrane antigen. *Angewandte Chemie* (International ed.) 2011, 50(39):9167-9170.

Banerjee, S. R.; Pullambhatla, M.; Shallal, H.; Lisok, A.; Mease, R. C.; Pomper, M. G. A modular strategy to prepare multivalent inhibitors of prostate-specific membrane antigen (PSMA). *Oncotarget* 2011; 2(12):1244-1253.

Barrett, J. A.; Coleman, R. E.; Goldsmith, S. J. et al. First-in-man evaluation of 2 high-affinity PSMA-avid small molecules for imaging prostate cancer. *J Nucl Med.* 2013; 54(3):380-387.

Barton, K. N.; Stricker, H.; Brown, S. L. et al. Phase I study of noninvasive imaging of adenovirus-mediated gene expression in the human prostate. *Mol Ther.* 2008, 16(10):1761-1769.

Bauer S, Kirschning C J, Hacker H, Redecke V, Hausmann S, Akira S, Wagner H, Lipford G B. Human TLR9 confers responsiveness to bacterial DNA via species-specific CpG motif recognition. *Proceedings of the National Academy of Sciences of the United States of America* 2001; 98(16):9237-9242.

Beeres, S. L.; Bengel, F. M.; Bartunek, J. et al. Role of imaging in cardiac stem cell therapy. *J. Am. Coll. Cardiol.* 2007, 49(11):1137-1148.

Brader, P.; Serganova, I.; Blasberg, R. G. Noninvasive molecular imaging using reporter genes. *J Nucl Med.* 2013, 54(2):167-172.

Campbell, D. O.; Yaghoubi, S. S.; Su, Y. et al. Structure-guided engineering of human thymidine kinase 2 as a positron emission tomography reporter gene for enhanced phosphorylation of non-natural thymidine analog reporter probe. *The J Biol. Chem.* 2012, 287(1):446-454.

Chang, S. S.; O'Keefe, D. S.; Bacich, D. J.; Reuter, V. E.; Heston, W. D.; Gaudin, P. B. Prostate-specific membrane antigen is produced in tumor-associated neovasculature. *Clin Cancer Res.* 1999; 5(10):2674-2681.

Chen, Y.; Dhara, S.; Banerjee, S. R. et al. A low molecular weight PSMA-based fluorescent imaging agent for cancer. *Biochem. Biophys. Res. Comm.* 2009, 390(3):624-629.

Chen, Y.; Foss, C. A.; Byun, Y. et al. Radiohalogenated prostate-specific membrane antigen (PSMA)-based ureas as imaging agents for prostate cancer. *J Med. Chem.* 2008, 51(24):7933-7943.

Chen, Y.; Pullambhatla, M.; Foss, C. A. et al. 2-(3-{1-Carboxy-5-[(6-[$^{18}$F]fluoropyridine-3-carbonyl)-amino]-pentyl}-ureido)-pentanedioic acid, [$^{18}$F]DCFPyL, a PSMA-based PET imaging agent for prostate cancer. *Clin Cancer Res.* 2011, 17(24):7645-7653.

Cho, S. Y.; Gage, K. L.; Mease, R. C. et al. Biodistribution, tumor detection, and radiation dosimetry of $^{18}$F-DCFBC, a low-molecular-weight inhibitor of prostate-specific membrane antigen, in patients with metastatic prostate cancer. *J Nucl Med.* 2012, 53(12):1883-1891.

De la Vieja, A.; Ginter, C. S.; Carrasco, N. Molecular analysis of a congenital iodide transport defect: G543E impairs maturation and trafficking of the Na+/I– symporter. *Mol. Endocrinol.* 2005, 19(11):2847-2858.

Dingli, D.; Kemp, B. J.; O'Connor, M. K.; Morris, J. C.; Russell, S. J.; Lowe, V. J. Combined 1-124 positron emission tomography/computed tomography imaging of NIS gene expression in animal models of stably transfected and intravenously transfected tumor. *Mol Imaging Biol.* 2006; 8(1):16-23.

FDA. Points to consider on plasmid DNA vaccines for preventive infectious disease indications. *Center for Biologics Evaluation and Research* 1996; Docket No.: 96N-0400.

Forss-Petter S, Danielson P E, Catsicas S, et al. Transgenic mice expressing betagalactosidase in mature neurons under neuron-specific enolase promoter control. *Neuron* 1990, 5:187-197.

Gil, J. S.; Machado, H. B.; Herschman, H. R. A method to rapidly and accurately compare the relative efficacies of non-invasive imaging reporter genes in a mouse model and its application to luciferase reporters. *Mol Imaging Biol.* 2012, 14(4):462-471.

Grant, C. L.; Caromile, L. A.; Ho, V. et al. Prostate specific membrane antigen (PSMA) regulates angiogenesis independently of VEGF during ocular neovascularization. *PloS One* 2012, 7(7):e41285.

Haberkorn, U. Gene therapy with sodium/iodide symporter in hepatocarcinoma. *Exp Clin Endocrinol Diabetes.* 2001, 109(1):60-62.

Heston, W. D. Characterization and glutamyl preferring carboxypeptidase function of prostate specific membrane antigen: a novel folate hydrolase. *Urology* 1997, 49(3A Suppl):104-112.

Hoti, N.; Li, Y.; Chen, C. L. et al. Androgen receptor attenuation of Ad5 replication: implications for the development of conditionally replication competent adenoviruses. *Mol Ther.* 2007, 15(8):1495-1503.

Ilies, M. A.; Seitz, W. A.; Ghiviriga, I. et al. (2004) Pyridinium cationic lipids in gene delivery: a structure-activity correlation study. *J Med Chem* 2004, 47:3744-3754.

Johnson, M.; Huyn, S.; Burton, J.; Sato, M.; Wu, L. Differential biodistribution of adenoviral vector in vivo as monitored by bioluminescence imaging and quantitative polymerase chain reaction. *Hum. Gene Ther.* 2006; 17(12):1262-1269.

Likar, Y.; Zurita, J.; Dobrenkov, K. et al. A new pyrimidine-specific reporter gene: a mutated human deoxycytidine kinase suitable for PET during treatment with acycloguanosine-based cytotoxic drugs. *J Nucl Med.* 2010, 51(9):1395-1403.

Liu, H.; Rajasekaran, A. K.; Moy, P. et al. Constitutive and antibody-induced internalization of prostate-specific membrane antigen. *Cancer Res.* 1998, 58(18):4055-4060.

Luo, J.; Deng, Z. L.; Luo, X. et al. A protocol for rapid generation of recombinant adenoviruses using the AdEasy system. *Nature Protocols.* 2007, 2(5):1236-1247.

Mease, R. C.; Dusich, C. L.; Foss, C. A. et al. N—[N—[(S)-1,3-Dicarboxypropyl]carbamoyl]-4-[$^{18}$F]fluorobenzyl-L-cysteine, [$^{18}$F]DCFBC: a new imaging probe for prostate cancer. *Clin Cancer Res.* 2008; 14(10):3036-3043.

Min, J. J.; Iyer, M.; Gambhir, S. S. Comparison of [$^{18}$F] FHBG and [$^{14}$C]FIAU for imaging of HSV1-tk reporter gene expression: adenoviral infection vs stable transfection. *Eur. J. Nucl. Med. Mol. I.* 2003, 30(11):1547-1560.

Miyagawa, M.; Anton, M.; Wagner, B. et al. Non-invasive imaging of cardiac transgene expression with PET: comparison of the human sodium/iodide symporter gene and HSV1-tk as the reporter gene. *Eur. J. Nucl. Med. Mol. I.* 2005; 32(9):1108-1114.

Mlcochova, P.; Barinka, C.; Tykvart, J.; Sacha, P.; Konvalinka, J. Prostate-specific membrane antigen and its truncated form PSM'. *The Prostate.* 2009, 69(5):471-479.

Overbeek P A, Chepelinsky A B, Khillan J S, Piatigorsky J, Westphal H. Lens-specific expression and developmental regulation of the bacterial chloramphenicol acetyltransferase gene driven by the murine alpha A-crystallin promoter in transgenic mice. *Proc. Natl. Acad. Sci. U.S.A.* 1985, 82:7815-7819.

Ponde, D. E.; Dence, C. S.; Schuster, D. P.; Welch, M. J. Rapid and reproducible radiosynthesis of [$^{18}$F] FHBG. *Nucl. Med. Biol.* 2004, 31(1):133-138.

Ponomarev, V.; Doubrovin, M.; Shavrin, A. et al. A human-derived reporter gene for noninvasive imaging in humans: mitochondrial thymidine kinase type 2. *J Nucl Med.* 2007; 48(5):819-826.

Rajasekaran, A. K.; Anilkumar, G.; Christiansen, J. J. Is prostate-specific membrane antigen a multifunctional protein? *Am. J. Physiol.* 2005, 288(5):C975-981.

Rajasekaran, S. A.; Anilkumar, G.; Oshima, E. et al. A novel cytoplasmic tail MXXXL motif mediates the internalization of prostate-specific membrane antigen. *Mol. Biol. Cell* 2003; 14(12):4835-4845.

Tjuvajev, J. G.; Doubrovin, M.; Akhurst, T. et al. Comparison of radiolabeled nucleoside probes (FIAU, FHBG, and FHPG) for PET imaging of HSV1-tk gene expression. *J Nucl Med.* 2002; 43(8):1072-1083.

van der Woude, I.; Wagenaar, A.; Meekel, A. A. et al. Novel pyridinium surfactants for efficient, nontoxic in vitro gene delivery. *Proc Natl Acad Sci USA* 1997, 94:1160-1165.

Yaghoubi, S. S.; Barrio, J. R.; Dahlbom, M. et al. Human pharmacokinetic and dosimetry studies of [(18)F]FHBG: a reporter probe for imaging herpes simplex virus type-1 thymidine kinase reporter gene expression. *J Nucl Med.* 2001, 42(8):1225-1234.

Yaghoubi, S. S.; Campbell, D. O.; Radu, C. G.; Czernin, J. Positron emission tomography reporter genes and reporter probes: gene and cell therapy applications. *Theranostics* 2012, 2(4):374-391.

Yaghoubi, S. S.; Gambhir, S. S. Measuring herpes simplex virus thymidine kinase reporter gene expression in vitro. *Nat. Protoc.* 2006, 1(4):2137-2142.

Yao, V.; Berkman, C. E.; Choi, J. K.; O'Keefe, D. S.; Bacich, D. J. Expression of prostate-specific membrane antigen (PSMA), increases cell folate uptake and proliferation and suggests a novel role for PSMA in the uptake of the non-polyglutamated folate, folic acid. *The Prostate* 2010; 70(3):305-316.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for using prostate-specific membrane antigen (PSMA) as an imaging reporter, the method comprising:
   a) introducing a CpG-free reporter gene construct comprising a CpG-free PSMA gene operably linked to a transcriptional promoter to a cell;
   b) allowing the cell to express PSMA protein, wherein the PSMA protein is mutated such that its second amino acid is glycine instead of tryptophan;
   c) adding an imaging probe that can detect the PSMA protein on a cell surface or inside the cell; and
   d) imaging the imaging probe, thereby detecting the PSMA protein, wherein the CpG-free reporter gene construct is a non-viral, episomal reporter gene construct, and further wherein the transcriptional promoter is a PEG-Promoter.

2. The method of claim 1, wherein the cell is a cancer cell.

3. The method of claim 1, wherein the non-viral, episomal reporter gene construct further comprises a Gal4-VP16 and Upstream Activation Sequence (UAS) transcriptional amplification system.

4. The method of claim 3, wherein the transcriptional amplification system comprises five copies of the UAS.

5. The method of claim 1, wherein the non-viral, episomal reporter gene construct further comprises the EBNA-1 gene.

6. The method of claim 1, wherein the non-viral, episomal reporter gene construct further comprises OriP.

7. The method of claim 1, wherein the PSMA gene comprises the coding sequence of the full-length PSMA protein.

8. The method of claim 1, wherein the reporter gene construct comprising a PSMA gene further comprises a neomycin or kanamycin resistant gene.

9. The method of claim 1, wherein the imaging probe detects the PSMA protein by binding to the active site of the PSMA protein.

10. The method of claim 1, wherein the imaging probe is cleaved by the PSMA protein.

11. The method of claim 10, wherein cleavage of the imaging probe results in at least one cleavage product that is fluorescent and/or radioactive.

12. The method of claim 1, wherein the imaging probe is 2-(3-{1-carboxy-5-[(6-[$^{18}$F]fluoro-pyridine-3-carbonyl)-amino]-pentyl}-ureido)-pentanedioic acid (DCFPyL) or N—[N—[(S)-1,3-dicarboxypropyl]carbamoyl]-4-[$^{18}$F]fluorobenzyl-L-cysteine (DCFBC).

13. The method of claim 1, wherein imaging the PSMA protein occurs by at least one method selected from the group consisting of near-infrared (NIR) optical tomography, positron emission tomography (PET), and single photon emission computed tomography (SPECT).

14. The method of claim 1, wherein the PSMA protein is detected on the surface of the cell.

15. The method of claim 1, wherein the PSMA protein is detected inside the cell.

16. The method of claim 1, wherein the cell is found in a subject.

17. The method of claim 16, wherein the subject is human.

* * * * *

SEQUENCE LISTING

<160> NUMBER OF SEQ ID NOS: 5

<210> SEQ ID NO 1
<211> LENGTH: 17
<212> TYPE: DNA
<213> ORGANISM: Artificial Sequence
<220> FEATURE:
<223> OTHER INFORMATION: Upstream activation sequence

<400> SEQUENCE: 1
yggagtactg tcctccg                                                17

<210> SEQ ID NO 2
<211> LENGTH: 95
<212> TYPE: DNA
<213> ORGANISM: Artificial Sequence
<220> FEATURE:
<223> OTHER INFORMATION: UAS sequence (5 copies)

<400> SEQUENCE: 2
cggagtactg tcctccgagc ggagtactgt cctccgagcg gagtactgtc ctccgagcgg    60
agtactgtcc tccgagcgga gtactgtcct ccgag                              95

<210> SEQ ID NO 3
<211> LENGTH: 31
<212> TYPE: DNA
<213> ORGANISM: Artificial Sequence
<220> FEATURE:
<223> OTHER INFORMATION: PCR primer

<400> SEQUENCE: 3
acgaagatct taatagtaat caattacggg g                                  31

<210> SEQ ID NO 4
<211> LENGTH: 31
<212> TYPE: DNA
<213> ORGANISM: Artificial Sequence
<220> FEATURE:
<223> OTHER INFORMATION: PCR primer

<400> SEQUENCE: 4
tccggaattc ctagcggatc tgacggttca c                                  31

<210> SEQ ID NO 5
<211> LENGTH: 2253
<212> TYPE: DNA
<213> ORGANISM: Homo sapiens

<400> SEQUENCE: 5
atgtggaatc tccttcatga aacagactct gctgtggcca cagccagaag acccagatgg    60
ctgtgtgctg gggccctggt gctggctggt ggcttctttc tcctgggctt cctctttggg   120
tggtttataa aatcctccaa tgaagctact aacattactc caaagcataa tatgaaagca   180
tttttggatg aattgaaagc tgagaacatc aagaagttct tatataattt tacacagata   240
ccacatttag caggaacaga acaaaacttt cagcttgcaa agcaaattca atcccagtgg   300
aaagaatttg gcctggattc tgttgagcta gcacattatg atgtcctgtt gtcctaccca   360
aataagactc atcccaacta catctcaata attaatgaag atggaaatga gattttcaac   420
acatcattat ttgaaccacc tcctccagga tatgaaaatg tttctgatat tgtaccacct   480
ttcagtgctt tctctcctca aggaatgcca gagggagata tagtgtatgt taactatgca   540
agaactgaag acttctttaa attggaaagg gacatgaaaa tcaattgctc tgggaaaatt   600

```
gtaattgcca gatatgggaa agttttcaga ggaaataagg ttaaaaatgc ccagctggca      660
ggggccaaag gagtcattct ctactctgac cctgctgact actttgctcc tggggtgaag      720
tcctatccag atggttggaa tcttcctgga ggtggtgtcc agagaggaaa tatcctaaat      780
ctgaatggtg caggagaccc tctcacacca ggttacccag caaatgaata tgcttatagg      840
agaggaattg cagaggctgt tggtcttcca agtattcctg ttcatccaat tggatactat      900
gatgcacaga agctcctaga aaaaatgggt ggctcagcac caccagatag cagctggaga      960
ggaagtctca aagtgcccta caatgttgga cctggcttta ctggaaactt ttctacacaa     1020
aaagtcaaga tgcacatcca ctctaccaat gaagtgacaa gaatttacaa tgtgataggt     1080
actctcagag gagcagtgga accagacaga tatgtcattc tgggaggtca cagggactca     1140
tgggtgtttg gtggtattga ccctcagagt ggagcagctg ttgttcatga aattgtgagg     1200
agctttggaa cactgaaaaa ggaagggtgg agacctagaa gaacaatttt gtttgcaagc     1260
tgggatgcag aagaatttgg tcttcttggt tctactgagt gggcagagga gaattcaaga     1320
ctccttcaag agagggagt ggcttatatt aatgctgact catctataga aggaaactac     1380
actctgagag ttgattgtac acccctgatg tacagcttgg tacacaacct aacaaaagag     1440
ctgaaaagcc ctgatgaagg cttttgaaggc aaatctcttt atgaaagttg gactaaaaaa     1500
agtccttccc cagagttcag tggcatgccc aggataagca aattgggatc tggaaatgat     1560
tttgaggtgt tcttccaaag acttggaatt gcttcaggca gagcaaggta tactaaaaat     1620
tgggaaacaa acaaattcag tggctatcca ctgtatcaca gtgtctatga aacatatgag     1680
ttggtggaaa agttttatga tccaatgttt aaatatcacc tcactgtggc ccaggttaga     1740
ggagggatgg tgtttgagct agccaattcc atagtgctcc cttttgattg tagagattat     1800
gctgtagttt taagaaagta tgctgacaaa atctacagta tttctatgaa acatccacag     1860
gaaatgaaga catacagtgt atcatttgat tcactttttt ctgcagtaaa gaattttaca     1920
gaaattgctt ccaagttcag tgagagactc caggactttg acaaaagcaa cccaatagta     1980
ttaagaatga tgaatgatca actcatgttt ctggaaagag catttattga tccattaggg     2040
ttaccagaca ggccttttta taggcatgtc atctatgctc caagcagcca aacaagtat       2100 gcaggggagt cattcccagg aatttatgat gctctgtttg atattgaaag caaagtggac     2160
ccttccaagg cctggggaga agtgaagaga cagatttatg ttgcagcctt cacagtgcag     2220
gcagctgcag agactttgag tgaagtagcc taa                                   2253
```